United States Patent
Yoshimura et al.

(10) Patent No.: US 8,283,162 B2
(45) Date of Patent: Oct. 9, 2012

(54) ANTIBODIES RELATING TO PIVKAII AND USES THEREOF

(75) Inventors: Toru Yoshimura, Matsudo (JP); Barry L. Dowell, Mundelein, IL (US); Gangamani S. Beligere, Grayslake, IL (US); Qiaoqiao Ruan, Round Lake, IL (US)

(73) Assignee: Abbott Laboratories, Abbott Park, IL (US)

( * ) Notice: Subject to any disclaimer, the term of this patent is extended or adjusted under 35 U.S.C. 154(b) by 318 days.

(21) Appl. No.: 12/401,361

(22) Filed: Mar. 10, 2009

(65) Prior Publication Data

US 2010/0233175 A1    Sep. 16, 2010

(51) Int. Cl.
  *C12N 5/07*  (2010.01)
  *C07K 1/00*  (2006.01)
  *C07H 21/02*  (2006.01)
(52) U.S. Cl. ............... 435/326; 530/388.1; 536/23.1
(58) Field of Classification Search .................. None
  See application file for complete search history.

(56) References Cited

U.S. PATENT DOCUMENTS

| | | |
|---|---|---|
| 4,526,938 A | 7/1985 | Churchill et al. |
| 4,880,078 A | 11/1989 | Inoue et al. |
| 4,980,286 A | 12/1990 | Morgan et al. |
| 5,006,309 A | 4/1991 | Khalil et al. |
| 5,063,081 A | 11/1991 | Cozzette et al. |
| 5,089,424 A | 2/1992 | Khalil et al. |
| 5,128,326 A | 7/1992 | Balazs et al. |
| 5,290,540 A | 3/1994 | Prince et al. |
| 5,624,821 A | 4/1997 | Winter et al. |
| 5,648,260 A | 7/1997 | Winter et al. |
| 5,679,377 A | 10/1997 | Bernstein et al. |
| 5,705,330 A | 1/1998 | Shah et al. |
| 5,714,350 A | 2/1998 | Co et al. |
| 5,855,913 A | 1/1999 | Hanes et al. |
| 5,874,064 A | 2/1999 | Edwards et al. |
| 5,912,015 A | 6/1999 | Bernstein et al. |
| 5,912,120 A | 6/1999 | Goldstein et al. |
| 5,916,597 A | 6/1999 | Lee et al. |
| 5,934,272 A | 8/1999 | Lloyd et al. |
| 5,985,309 A | 11/1999 | Edwards et al. |
| 5,985,320 A | 11/1999 | Edwards et al. |
| 5,989,463 A | 11/1999 | Tracy et al. |
| 6,019,968 A | 2/2000 | Platz et al. |
| 6,350,861 B1 | 2/2002 | Co et al. |
| 6,660,843 B1 | 12/2003 | Feige et al. |
| 7,612,181 B2 | 11/2009 | Wu et al. |
| 2002/0137134 A1 | 9/2002 | Gerngross |
| 2003/0170881 A1 | 9/2003 | Davis et al. |
| 2004/0018577 A1 | 1/2004 | Emerson Campbell et al. |
| 2004/0018590 A1 | 1/2004 | Gerngross et al. |
| 2005/0042664 A1 | 2/2005 | Wu et al. |
| 2005/0054078 A1 | 3/2005 | Miller et al. |
| 2006/0104968 A1 | 5/2006 | Bookbinder et al. |
| 2006/0160164 A1 | 7/2006 | Miller et al. |

FOREIGN PATENT DOCUMENTS

| | | | |
|---|---|---|---|
| EP | 8411011.8 | * | 5/1985 |
| EP | 0182495 | A1 | 5/1986 |
| EP | 1176195 | A1 | 1/2002 |
| JP | 09249699 | | 9/1997 |
| WO | WO-9005144 | A1 | 5/1990 |
| WO | WO-9105548 | A1 | 5/1991 |
| WO | WO-9219244 | A2 | 11/1992 |
| WO | WO-9620698 | A2 | 7/1996 |
| WO | WO-9732572 | A2 | 9/1997 |
| WO | WO-9744013 | A1 | 11/1997 |
| WO | WO-9831346 | A1 | 7/1998 |
| WO | WO-9915154 | A1 | 4/1999 |
| WO | WO-9920253 | A1 | 4/1999 |
| WO | WO-9925044 | A1 | 5/1999 |
| WO | WO-9954342 | A1 | 10/1999 |
| WO | WO-9966903 | A2 | 12/1999 |
| WO | WO-0037504 | A2 | 6/2000 |
| WO | WO-0183525 | A2 | 11/2001 |
| WO | WO-02072636 | A2 | 9/2002 |
| WO | WO-03016466 | A2 | 2/2003 |
| WO | WO-03035835 | A2 | 5/2003 |
| WO | WO-2004067561 | A1 | 8/2004 |
| WO | WO-2004078140 | A2 | 9/2004 |
| WO | WO-2005100584 | A2 | 10/2005 |

OTHER PUBLICATIONS

Naraki et al (Biochimica et Biophysica Acta, 2002, 287-298).*
Matsuda et al (European Application 8411011.8, 1985).*
Bird et al (Science, 1998, 242: 423-426).*
Sakaguchi et al (Journal of Immunology, 2005, 174: 4485-4494).*
Burgess et al. (J. Cell Biol. 111:2129-2138, 1990).*
Lazar et al. ( Mol. Cell Biol. 8:1247-1252, 1998).*
Altschuel, et al., "Gapped BLAST and PSI-BLAST: a new generation of protein database search programs," Nucl. Acid Res, 1997, 25 (17), 3389-3402.
Annis I., et al., "Disulfide bond formation in peptides," Methods Enzymol, 1997, 289, 198-221.
Ausubel F. M., et al., "Current Protocols in Molecular Biology," 1987, John Wiley & Sons.
Bajaj S. P., et al., "Decarboxylation of gamma-carboxyglutamic acid residues in human prothrombin. Stoichiometry of calcium binding to gamma-carboxyglutamic acid in prothrombin," J Biol Chem, 1982, 257 (7), 3726-31.
Bird, et al., "Single-Chain Antigen Binding Proteins," Science, 1988, 242, 423-426.
Buchwald H., et al., "Long-term, continuous intravenous heparin administration by an implantable infusion pump in ambulatory patients with recurrent venous thrombosis," Surgery, 1980, 88, 507-516.
Chothia C., et al., "Canonical Structures for the Hypervariable Regions of Immunoglobulins," J. Mol. Biol, 1987, 196, 901-917.
Chothia C., et al., "Conformations of immunoglobulin hypervariable regions," Nature, 1989, 342, 877-883.
Chothia C., et al., "Structural Repertoire of the Human VH Segments," J. Mol. Biol., 1992, 227, 799-817.

(Continued)

Primary Examiner — Sean Aeder
(74) Attorney, Agent, or Firm — Cheryl L. Becker

(57) ABSTRACT

The present invention relates to antibodies that may be used, for example, in the diagnosis, treatment and prevention of haepatocellular carcinoma (HCC), liver cancer and related conditions.

10 Claims, 8 Drawing Sheets

OTHER PUBLICATIONS

Cleek R. L., et al., "Biodegradable Polymeric Carriers for a bFGF Antibody for Cardiovascular Application," Proc. Intl. Symp. Control. Rel. Bioact. Mater, 1977, 24, 853-854.

Co M. S., et al., "Genetically Engineered Deglycosylation of the Variable Domain Increases the Affinity of an Anti-CD33 Monoclonal Antibody," Molec. Immunol, 1993, 30 (15), 1361-1367.

Durazo, et al., "Des-gamma-carboxyprothrombin, alpha-fetoprotein and AFP-L3 in patients with chronic hepatitis, cirrhosis and hepatocellular carcinoma," J Gastroenterol Hepatol, 2008, 23 (10), 1541-1548.

During M. J., et al., "Controlled Release of Dopamine from a Polymeric Brain Implant: In Vivo Characterization," Ann. Neurol, 1989, 25, 351-356.

Durocher Y., et al., "High-level and high-throughput recombinant protein production by transient transfection of suspension-growing human 293-EBNAI cells," Nucl Acids. Res., 2002, 30 (2), e9.

Foote J., et al., "Antibody Framework Residues Affecting the Conformation of the Hypervariable Loops," J. Mol. Biol., 1992, 224, 487-489.

Fujiyama S., et al., "Clinical evaluation of plasma abnormal prothrombin (PIVKA-II) in patients with hepatocellular carcinoma," Hepatogastroenterology, 1986, 33 (5), 201-205.

Giege R., et al., "An introduction to the crystallogenesis of biological macromolecules," in: Crystallization of Nucleic Acids & Proteins, a Practical Approach, Ducruix A., 1999, 2, 201-16.

Goldspiel B. R., et al., "Human gene therapy," Clin. Pharm., 1993, 12, 488-505.

Goodson, "Medical Applications of Controlled Release Technology," Langer and Wise, Eds., 1984, 2, 115-138.

Hammerlin, et al., "Monoclonal Antibodies and T-Cell Hybridomas," 1981, 563-681.

Harlow E., et al., "Antibodies: A Laboratory Manual," Table of Contents, 1988, Cold Spring Harbor Laboratory Press.

Herai, et al., ""Evaluation of PIVKA-II Assay by Chemiluminescent Enzyme immunoassay and its Clinical Usefulness in Hepatocellular Carcinoma,"" Japanese J Clinical Laboratory Automation, 2007, 32 (2), 205-210.

Higgins D. G., et al., "Fast and sensitive multiple sequence alignments on a microcomputer," CABIOS Comm., 1989, 5 (2), 151-153.

Holliger P., et al., ""Diabodies": Small bivalent and Bispecific Antibody Fragments," PNAS USA, 1993, 90, 6444-6448.

Howard III, M. A., et al., "Intracerebral drug delivery in rats with lesion-induced memory deficits," J. Neurosurg., 1989, 71, 105-112.

Huston, et al., "Protein Engineering of Antibody Binding Sites: Recovery of Specific Activity in an Anti-Digoxin Single-Chain Fv Analogue Produced in *Escherichia coli*," PNAS USA, 1988, 85 (16), 5879-5883.

Ishida T., et al., "Percutaneous Microwave Tumor Coagulation for Hepatocellular Carcinomas with Interruption of Segmental Hepatic Blood Flow," J. Vasc. Interv. Radiol, 2002, 13, 185-191.

Jefferis R., "Glycosylatoin of Recombinant antibody Therapeutics," Biotechnol. Prog., 2005, 21, 11-16.

Johnsson B., et al., "Comparison of Methods for Immobilizatoin to Carboxymethyl Dextran Sensor Surfaces by Analysis of the Specific Activity of Monoclonal Antibodies," J. Molecular Recog, 1995, 8, 125-131.

Johnsson B., et al., "Immobilization of Proteins to a Carboxymethyldextran-Modified Gold Surface for Biospecific Interaction Analysis I Surface Plasmon Resonance Sensors," Analyt. Biochem., 1991, 198, 268-277.

Joliot A., et al., "Antennapedia homeobox peptide regulates neural morphogenesis," PNAS USA, 1991, 88, 1864-1868.

Jonsson U., et al., "Introducing a biosensor based technology for real-time biospecific interaction analysis", Ann. Biol. Clin., (1993), 51, 19-26.

Jonsson U., et al., "Real-Time Biospecific Interaction Analysis Using Surface Plasmon Resonance and a Sensor Chip Technology," BioTechniques, 1991, 11 (5), 620-627.

Kabat E. A., et al., "Attempts to Locate Complementarity-Determining Residues in the variable Positions of Light and Heavy Chains," Ann, NY Acad. Sci,1971, 190, 382-391.

Kabat E. A., et al., "Sequences of Proteins of Immunological Interest," NIH Publ. #91, 1981, 5, Table of Contents.

Kabat, et al., "Sequences of Proteins of Immunological Interest, Bethesda, MD 1987,1991," National Institutes of Health, 1991, 1.

Kaufman R. J., et al., "Amplification and Expression of Sequences Cotransfected with a Modular Dihydrofolate Reductase Complementary DNA Gene," J. Mol. Biol., 1982, 159, 601-621.

Kipriyanov S. M., et al., "Recombinant Single-Chain Fv Fragments Carrying C-Terminal Cysteine Residues: Production of Bivlent and Biotinylated Miniantibodies," Molecular Immunology, 1994, 31, 1047-1058.

Kipriyanov S. M., et al., "Single-chain Antibody Streptavidin Fusions: Tetrameric Bifunctional scFv-Complexes with Biotin Binding Activity and Enhanced Affinity to Antigen," Human Antibodies and Hybridomas, 1995, 6, 93-101.

Kontermann D., ed., Antibody Engineering, Table of Contents., 2001.

Kriegler M., Gene Transfer and Expression: A Laboratory Manual, Stockton Press, Table of Contents, 1990.

Lam X. M., et al., "Microencapsulation of Recombinant Humanized Monoclonal Antibody for Local Delivery," Procelna Symp. Control. Rel. Bioact. Mater., 1997, 24, 759-760.

Langer R., "New Methods of Drug Delivery," Science, 1990, 249, 1527-1533.

Langer R., et al., "Chemical and Physical Structure of Polymers as Carriers for Controlled Release of Bioactive Agents: A Review," J of Macromolecular Science, Part C: Polymer Reviews, 1983, 23, 61-126.

Levy, et al., "Inhibition of Calcification of Bioprosthetic Heart Valves by Local Controlled-Release Diphosphonate," Science, 1985, 228, 190-192.

Liebman H. A., et al., "Des-gamma-carboxy (abnormal) prothrombin as a serum marker of primary hepatocellular carcinoma," N Engl J Med, 1984, 310 (22), 1427-1431.

MacCallum, et al., "Antibody-antigen Interactions: Contact Analysis and Binding Site Topography," J. Mol. Biol., 1996, 262 (5), 732-745.

Marrero J. A., et al., "Des-gamma carboxyprothrombin can differentiate hepatocellular carcinoma from nonmalignant chronic liver disease in american patients," Hepatology, 2003, 37 (5), 1114-1121.

Mizushima S., et al., "pEF-BOS, a powerful mammalian expression vector," Nucl. Acids Res., 18 (17), 5322.

Morgan R. A., et al., "Human Gene Therapy," Ann. Rev. Biochem., 1993, 62, 191-217.

Mulligan R. C., "The Basic Science of Gene Therapy," Science, 1993, 260, 926-932.

Naraki T., et al., "gamma-Carboxyglutamic acid content of hepatocellular carcinoma-associated des-gamma-carboxy prothrombin," Biochim Biophys Acta, 2002, 1586 (3), 287-298.

Needleman S. B., et al., "A General Method Applicable to the Search for Similarities in the Amino Acid Sequence of Two Proteins," J Mol Biol, 1970, 48, 443-453.

Ning S., et al., "Intratumoral radioimmunotherapy of a human colon cancer xenograft using a sustained-release gel," Radiotherapy & Oncology, 1996, 39, 179-189.

Padlan E. A., et al., "Identification of specificity-determining residues in antibodies," FASEB 1, 1995, 9, 133-139.

Pearson W. R., et al., "Improved tools for biological sequence comparison," PNAS USA, 1988, 85, 2444-2448.

Poljak R. J., et al., "Production and Structure of Diabodies," Structure, 1994, 2, 1121-1123.

Remington, "Pharmaceutical Sciences and Introduction to Pharmaceutical Dosage Forms," 1995, 19, Mack Pub. Co.

Robinson J. R., Ed., Sustained and Controlled Release Drug Delivery Systems, Marcel Dekker, New York (1978).

Robinson, "Gene therapy—proceeding from laboratory to clinic," TIBTECH, 1993, 11 (5), 155.

Sakaguchi, et. al., "Generation of high-affinity antibody against T cell-dependent antigen in the Ganp gene-transgenic mouse," J Immunol, 2005, 174 (8), 4485-4494.

Sambrook J., et al., "Molecular Cloning—A Laboratory Manual," 1989, 2, Cold Spring Harbor Laboratory Press, Table of Contents.

Saudek C. D., et al., "A Preliminary Trail of the Programmable Implantable Medication System for Insulin Delivery," New Engl. J. Med., 1989, 321 (9), 574-579.

Sefton M. V., "Implantable Pumps," Critical Reviews in Biomedical Engineering, 1987, 14 (3), 201-240.

Shields R. L., et al., "Lack of Fucose on Human IgG1 N-Linked Oligosaccharide Improves Binding to Human Fc[gamma]RIII and Antibody-dependent Cellular Toxicity," J. Biol. Chem., 2002, 277 (30), 26733-26740.

Smith, et al.,"Comparison of Biosequences", Adv. Appl. Math, 1981, 2, 482-489.

Smolen and Ball (Eds.), Controlled Drug Bioavailability, vol. 1: Drug Product Design and Performance, John Wiley & Sons, New York, Table of Contents, 1984.

Song Y. K., et al., "Antibody Mediated Lung Targeting of Long-Circulating Emulsions," PDA J. Pharm. Sci. & Tech, 1995, 50, 372-397.

Suzuki M., et al., "Des-gamma-carboxy prothrombin is a potential autologous growth factor for hepatocellular carcinoma," J Biol Chem, 2005, 280 (8), 6409-15.

Tetin S. Y., et al., "Interactions of two monoclonal antibodies with BNP: high resolution epitope mapping using fluorescence correlation spectroscopy," Biochemistry, 2006, 45 (47), 14155-65.

Tetin S.Y., et al., "Optical spectroscopy in studies of antibody-hapten interactions," Methods, 2000, 20 (3), 341-361.

Tolstoshev P., "Gene therapy, concepts, current trials and future directions," Annu Rev Pharmacol Toxicol, 1993, 33, 573-96.

Umana P., et al., "Engineered glycoforms of an antieuro-blastoma IgG1 with optimized antibody-dependent cellular cytotoxic activity," Nature Biotech., 1999, 17, 176-180.

Urlaub, et al., "Isolation of Chinese Hamster Cell Mutants Deficient in Dihydrofolate Reductase Activity," PNAS USA, 1980, 77, 4216-4220.

Wallick S. C., et al., "Glycosylation of a VH Residue of a Monoclonal Antibody Against a (1-46) Dextran Increases Its Affinity for Antigen," J. Exp. Med., 1988, 168, 1099-1109.

Ward E. S., et al., "Binding activities of a repertoire of single immunoglobulin variable domains secreted from *Escherichia coli*," Nature, 1989, 341, 544-546.

Wright A., et al., "Antibody variable region glycosylation: position effects on antigen binding and carbohydrate structure," The EMBO J., 1991, 10 (10), 2717-2723.

Wu G. Y., et al., "Delivery systems for gene therapy," Biotherapy, 1991, 3, 87-95.

Wu G.Y., et al., "Receptor-mediated in vitro gene transformation by a soluble DNA carrier system," J Biol Chem, 1987, 262 (10), 4429-32.

Yamaguchi I., et al., "Development of des-gamma-carboxy prothrombin (DCP) measuring reagent using the LiBASys clinical analyzer," Clin Chem Lab Med, 2008, 46 (3), 411-416.

Yuen M. F., et al., "Serological markers of liver cancer," Best Pract Res Clin Gastroenterol, 2005, 19 (1), 91-99.

International Search Report PCT/US/2010026599, dated Jul. 28, 2010.

Owens, et al, "Monoclonal Antibodies against Human Abnormal Prothrombin Specific for the Calciam free", Biological Chemistry, 13800-13805, 1994.

Sekiya, et al, "Characterstics of PIVKA",International IHepalogy Commission, vol. 2,277-284, 1994.

Sugimoto, et al, "DCP a noval parameter measured bymonoclonalantibodies MU-3 and 19B7", Liver International, vol. 23, 38-44, 2003.

* cited by examiner

| PIVKAII Gla domain (13-27) analogs | Apparent Diffusion Coefficient (D) um^2/sec |
|---|---|
| Positive Control | 174±10 |
| Negative Control | 47±4 |
| Protein C peptide | 53±5 |
| Protein S peptide | 50±5 |
| Protein Z peptide | 51±5 |
| Factor VII peptide | 49±5 |
| Factor IX peptide | 48±5 |
| Factor X peptide | 52±5 |

ANTIBODIES RELATING TO PIVKAII AND USES THEREOF

BACKGROUND OF THE INVENTION

1. Field of the Invention

The present invention relates to antibodies that may be used, for example, in the diagnosis, treatment and prevention of hepatocellular carcinoma (HCC), liver cancer and related conditions.

2. Background Information

PIVKA-II is a Prothrombin Induced Vitamin K Antagonist (PIVKA) specific to Factor II. The GLA domain of Prothromin II or Factor II undergoes a post-synthetic modification in the presence of Vitamin K wherein 10 glutamic acid amino acids in the GLA-domain are carboxylated to g-carboxy glutamic acid. The carboxylation process is abherent in the diseased state. Thus, PIVKAII is known to be elevated in the case of HCC patients (Liebman et. al., *The New England Journal of Medicine* (1984), 310 (22), pages 1427-1431; Fujiyama et. al., *Hepato-gastroenterology* (1986), 33, pages 201-205; Marreo et. al., Hepatology (2003), 37, pages 1114-1121).

At present, there are inefficient methods by which to detect HCC or liver cancer by use of biomarkers (Koteish et. al., *J. Vasc. Interv. Radiol.* (2002), 13, pages 185-190; Yuen et. al., *Best Practice & Research Clinical Gastroenterology* (2005), 19, pages 91-99; see also Herai et al., *Japanese Journal of Clinical Laboratory Automation* (2007), 32(2), pages 205-210; Durazo et al., *Journal of Gastroenterology and Hepatology* (2008), 23, pages 1541-1548; Yamaguchi et al., *Clin. Chem. Lab. Med.* (2008), 46(3), pages 411-416). Further, there are few monoclonal antibodies in existence that can be used in immunoassays to effectively detect such conditions or to treat such conditions (Naraki et. al., *Biochemica at Biophysica Acta* (2002), 1586, page 287-298). Thus, there is a tremendous need in oncology for the development of antibodies that can be used efficaciously for both purposes.

All patents and publications referred to herein are hereby incorporated in their entirety by reference.

SUMMARY OF THE INVENTION

The present invention pertains to binding proteins or monoclonal antibodies that may be used in the diagnosis a of HCC, liver cancer and related hepatic conditions. Further, the present invention also provides methods of producing and using these binding proteins (i.e., monoclonal antibodies) or portions thereof.

In particular, the subject invention encompasses a binding protein or antibody comprising an antigen-binding domain that binds to one or more epitopes of PIVKA-II. (The hybridoma producing the antibody referred to as 3C10, has been deposited with the American Type Culture Collection, 10901 University Boulevard, Manassas, Va. 20110-2209 on Nov. 25, 2008 and has received deposit designation PTA-9638 and is also encompassed within the scope of the present invention.)

More specifically, the present invention pertains to a binding protein (e.g., antibody) comprising an antigen-binding domain which binds to one or more epitopes of PIVKA-II, preferably amino acids 13-27 of PIVKA-II. The binding protein has a dissociation constant in the range of approximately $1.0 \times 10^{-9}$ M to $1.0 \times 10^{-11}$ M.

One aspect of the invention pertains to an isolated nucleic acid molecule encoding the binding protein disclosed above. Further, the invention includes a vector comprising the isolated nucleic acid disclosed above. The vector may be, for example, selected from the group consisting of pcDNA; pTT (Durocher et al., *Nucleic Acids Research* 2002, Vol 30, No. 2); pTT3 (pTT with additional multiple cloning site; pEFBOS (Mizushima, S. and Nagata, S., (1990) *Nucleic acids Research* Vol 18, No. 17); pBV; pJV; and pBJ.

Additionally, the present invention includes a host cell transformed with the vector disclosed above. Preferably, the host cell is a prokaryotic cell. More preferably, the host cell is *E. coli*. The host cell may also be a eukaryotic cell. Preferably, the eukaryotic cell is selected from the group consisting of a protist cell, an animal cell, a plant cell and a fungal cell. More preferably, the host cell is a mammalian cell including, but not limited to, a CHO cell or a COS cell, a fungal cell such as *Saccharomyces cerevisiae* or an insect cell such as Sf9.

The present invention also includes the amino acid sequence encoded by the nucleotide sequence referred to above as well as a variable heavy chain of an antibody, wherein this heavy chain comprises an amino acid sequence at least 70% identical to the amino acid sequence of the binding protein described herein.

Additionally, the present invention encompasses a method of producing a binding protein that binds to at least one epitope of PIVKA-II, comprising culturing any one of the host cells disclosed above in a culture medium under conditions and for a time sufficient to produce a binding protein that binds to at least one epitope of PIVKA-II and preferably amino acids 13-27 of PIVKA-II.

Also, the present invention includes a method of detecting PIVKA-II antigen in a test sample comprising the steps of: 1) contacting the test sample with a first antibody having an antigen-binding domain which binds to amino acids 13-27 of PIVKA-II for a time and under conditions sufficient for the formation of first antibody/antigen complexes; 2) adding a conjugate to the first antibody/antigen complexes, wherein the conjugate comprises a second antibody attached to a signal generating compound capable of generating a detectable signal, for a time and under conditions sufficient to form first antibody/antigen/second antibody complexes; and 3) detecting presence of a signal generating by said signal generating compound, presence of said signal indicating presence of PIVKA-II antigen in said test sample. The first antibody may comprise an antigen-binding domain that binds to amino acids 13-27 of PIVKA-II (e.g., 3C10). It may be produced by a hybridoma cell line having ATCC deposit designation PTA-9638.

Further, the invention also encompasses another method of detecting PIVKA-II antigen in a test sample. This method comprises the steps of: a) contacting PIVKA-II antigen with an antibody to PIVKA-II antigen for a time and under conditions sufficient to form PIVKA-II antigen/antibody complexes, wherein the antibody is labeled with a signal generating compound capable of generating a detectable signal; b) adding the test sample to the PIVKA-II antigen/antibody complexes for a time and under conditions sufficient to form PIVKA-II antigen/antibody/antigen complexes; and c) detecting presence of a signal generating by the signal generating compound, presence of the signal indicating presence of PIVKA-II antigens in the test sample. Again, the antibody to PIVKA-II antigen may comprise an antigen-binding domain that binds to amino acids 13-27 of PIVKA-II. Also, the antibody may be produced by a hybridoma cell line having ATCC deposit designation PTA-9638.

Moreover, the present invention includes a further method of detecting PIVKA-II antigen in a test sample. This method comprises the steps of: 1) contacting the test sample with a PIVKA-II reference antigen, wherein the antigen is attached to a signal generating compound capable of generating a detectable signal and an antibody to PIKVA-II antigen, for a time and under conditions sufficient to form PIVKA-II reference antigen/antibody complexes and b) detecting a signal generated by said signal generating compound, wherein the amount of PIVKA-II antigen detected in the test sample is inversely proportional to the amount of PIVKA-II reference antigen bound to the antibody. Again, the antibody may comprise an antigen-binding domain that binds to amino acids 13-27 of PIVKA-II. The antibody may be produced by a hybridoma cell line having ATCC deposit designation PTA-9638.

Additionally, the present invention includes a method of producing a hybridoma cell line that expresses a binding protein comprising an antigen binding domain which binds to amino acids 13-27 of PIVKA-II. This method comprises the steps of: 1) immunizing a GANP mouse with an antigen comprising amino acids 13-27 of PIVKA-II for a time and under conditions sufficient for the mouse to produce antibodies against the antigen; 2) harvesting and purifying B cells from the spleen of the mouse; 3) fusing the spleen cells with myeloma cells in order to produce hybridomas; and 4) selecting a hybridoma cell line which expresses the binding protein comprising an antigen binding domain which binds to amino acids 13-27 of PIVKA-II. The hybridoma cell line may be, for example that having ATCC deposit designation PTA-9638.

Furthermore, the present invention includes a pharmaceutical composition comprising the above-described binding protein and a pharmaceutically acceptable carrier.

Additionally, the present invention includes a method of diagnosing hepatocellular carcinoma (HCC) or liver cancer in a patient suspected of having one of these conditions. The method comprises the steps of: 1) isolating a biological sample from the patient; 2) contacting the biological sample with an antibody comprising an antigen binding domain that binds to amino acids 13-27 of PIVKA-II antigen for a time and under conditions sufficient for formation of PIVKA-II antigen/antibody complexes; 3) detecting presence of the PIVKA-II antigen/antibody complexes in the sample; 4) dissociating the PIVKA-II antigen present in the complexes from the antibody present in the complexes; and 5) measuring the amount of dissociated PIVKA-II antigen, wherein an amount of PIVKA-II antigen greater than approximately 40 mAU/mL indicates a diagnosis of HCC or liver cancer in the patient. (The dissociated PIVKA-II antigen may be measured, for example, by mass spectroscopy.) The present invention includes an additional method of diagnosing HCC or liver cancer in a patient suspected of having one of these conditions. This method comprises the steps of: 1) isolating a biological sample from the patient; 2) contacting the biological sample with a first antibody comprising an antigen bind domain that binds to amino acids 13-27 of PIVKA-II antigen for a time and under conditions sufficient for the formation of PIVKA-II antigen/antibody complexes; 3) adding a conjugate to the resulting PIVKA-II antigen/antibody complexes for a time and under conditions sufficient to allow the conjugate to bind to the bound PIVKA-II antigen, wherein the conjugate comprises a second antibody attached to a signal generating compound capable of generating a detectable signal; 4) detecting the presence of PIVKA-II antigen which may be present in the biological sample by detecting a signal generated by the signal generating compound; and 5) measuring the amount of PIVKA-II antigen present in the test sample by measuring the intensity of the signal, an amount of PIVKA-II antigen greater than approximately 40 mAU/mL indicating a diagnosis of HCC or liver cancer in said patient.

The present invention also includes a kit containing the binding protein described above or the monoclonal antibody produced by the hybridoma described above. The kit may also contain other components in addition to an instruction sheet.

DETAILED DESCRIPTION OF THE INVENTION

Figure 1:
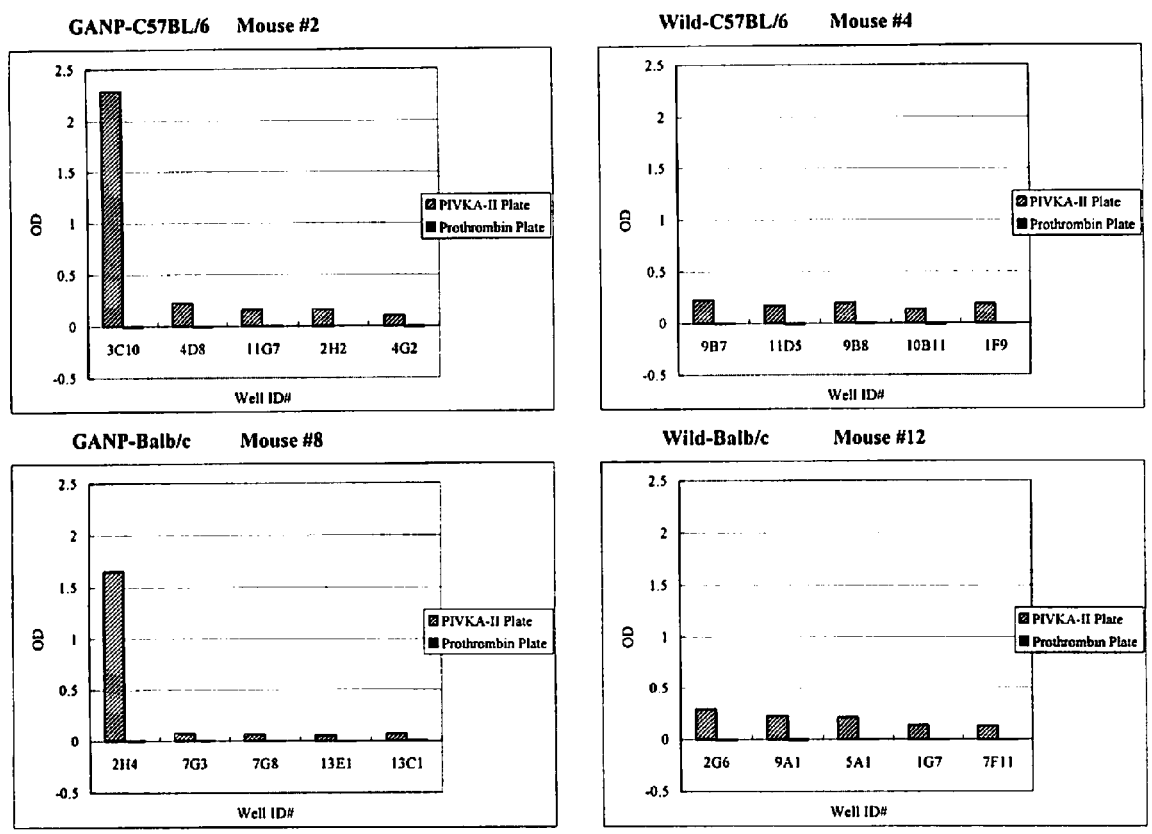
FIG. 1 illustrates the reactivity to PIVKA-II and Prothrombin in connection with the top, selected 5 hybridomas in each group. In particular, the panels show the reactivity of hybridomas from GANP transgenic mice or wild type mice to PIVKA-II and Prothrombin.

According to a particular embodiment, the invention relates to an antibody and, in particular, a monoclonal antibody that binds to one or more epitopes of PIVKA-II with a $K_D$ of $1 \times 10^{-7}$ M or less, and preferably in a range of $1 \times 10^{-7}$ M to $1 \times 10^{-11}$ M. In particular, the binding protein or antibody of the invention has a dissociation constant ($K_D$) to the 13-27 amino acid region of PIVKA-II of about $1 \times 10^{-9}$ or greater, preferably about $1 \times 10^{-10}$ or greater and more preferably about $1 \times 10^{-11}$ M or greater. The antibody is capable of specifically recognizing and binding to PIVKA-II. Once it is bound to PIVKA-II, it is not replaced by other PIVKAs such as, for example, PIVKA-VII, PIVKA-Protein C, PIVKA-Protein S, PIVKA-Protein and PIVKA-IX. In a situation in which the antibody is exposed to PIVKA-II and PIVKA-X at the same time, it is noteworthy that the 3C10 antibody of the present invention has a 10 times lower affinity to PIVKA-X than to PIVKA II.

The subject invention also includes isolated nucleotide sequences (and fragments thereof) encoding the variable light and heavy chains of the antibodies of the present invention as well as those nucleotide sequences (or fragments thereof) having sequences comprising, corresponding to, identical to, hybridizable to, or complementary to, at least about 70% (e.g., 70% 71%, 72%, 73%, 74%, 75%, 76%, 77%, 78% or 79%), preferably at least about 80% (e.g., 80%, 81%, 82%, 83%, 84%, 85%, 86%, 87%, 88% or 89%), and more preferably at least about 90% (e.g, 91%, 92%, 93%, 94%, 95%, 96%, 97%, 98%, 99% or 100%) identity to these encoding nucleotide sequences. (All integers (and portions thereof) between and including 70% and 100% are considered to be within the scope of the present invention with respect to percent identity.) Such sequences may be derived from any source (e.g., either isolated from a natural source, produced via a semi-synthetic route, or synthesized de novo). In particular, such sequences may be isolated or derived from sources other than described in the examples (e.g., bacteria, fungus, algae, mouse or human).

In addition to the nucleotide sequences described above, the present invention also includes amino acid sequences of the variable light and heavy chains of the antibodies described herein (or fragments of these amino acid sequences). Further, the present invention also includes amino acid sequences (or fragments thereof) comprising, corresponding to, identical to, or complementary to at least about 70% (e.g., 70%, 71%, 72%, 73%, 74%, 75%, 76%, 77%, 78% or 79%), preferably at least about 80% (e.g., 80% 81%, 82%, 83%, 84%, 85%, 86%, 87%, 88% or 89%), and more preferably at least about 90% identity (e.g., 90%, 91%, 92%, 93%, 94%, 95%, 96%, 97%, 98%, 99% or 100%), to the amino acid sequences of the proteins of the present invention. (Again, all integers (and portions thereof) between and including 70% and 100% (as recited in connection with the nucleotide sequence identities noted above) are also considered to be within the scope of the present invention with respect to percent identity.) For purposes of the present invention, a "fragment" of a nucleotide sequence is defined as a contiguous sequence of approximately at least 6, preferably at least about 8, more preferably at least about 10 nucleotides, and even more preferably at least about 15 nucleotides corresponding to a region of the specified nucleotide sequence.

The term "identity" refers to the relatedness of two sequences on a nucleotide-by-nucleotide basis over a particular comparison window or segment. Thus, identity is defined as the degree of sameness, correspondence or equivalence between the same strands (either sense or antisense) of two DNA segments (or two amino acid sequences). "Percentage of sequence identity" is calculated by comparing two optimally aligned sequences over a particular region, determining the number of positions at which the identical base or amino acid occurs in both sequences in order to yield the number of matched positions, dividing the number of such positions by the total number of positions in the segment being compared and multiplying the result by 100. Optimal alignment of sequences may be conducted by the algorithm of Smith & Waterman, Appl. Math. 2:482 (1981), by the algorithm of Needleman & Wunsch, J. Mol. Biol. 48:443 (1970), by the method of Pearson & Lipman, Proc. Natl. Acad. Sci. (USA) 85:2444 (1988) and by computer programs which implement the relevant algorithms (e.g., Clustal Macaw Pileup; Higgins et al., CABIOS. 5L151-153 (1989)), FASTDB (Intelligenetics), BLAST (National Center for Biomedical Information; Altschul et al., Nucleic Acids Research 25:3389-3402 (1997)), PILEUP (Genetics Computer Group, Madison, Wis.) or GAP, BESTFIT, FASTA and TFASTA (Wisconsin Genetics Software Package Release 7.0, Genetics Computer Group, Madison, Wis.). (See U.S. Pat. No. 5,912,120.)

For purposes of the present invention, "complementarity" is defined as the degree of relatedness between two DNA segments. It is determined by measuring the ability of the sense strand of one DNA segment to hybridize with the antisense strand of the other DNA segment, under appropriate conditions, to form a double helix. A "complement" is defined as a sequence which pairs to a given sequence based upon the canonic base-pairing rules. For example, a sequence A-G-T in one nucleotide strand is "complementary" to T-C-A in the other strand.

In the double helix, adenine appears in one strand, thymine appears in the other strand. Similarly, wherever guanine is found in one strand, cytosine is found in the other. The greater the relatedness between the nucleotide sequences of two DNA segments, the greater the ability to form hybrid duplexes between the strands of the two DNA segments.

"Similarity" between two amino acid sequences is defined as the presence of a series of identical as well as conserved amino acid residues in both sequences. The higher the degree of similarity between two amino acid sequences, the higher the correspondence, sameness or equivalence of the two sequences. ("Identity between two amino acid sequences is defined as the presence of a series of exactly alike or invariant amino acid residues in both sequences.) The definitions of "complementarity", "identity" and "similarity" are well known to those of ordinary skill in the art.

"Encoded by" refers to a nucleic acid sequence which codes for a polypeptide sequence, wherein the polypeptide sequence or a portion thereof contains an amino acid sequence of at least 3 amino acids, more preferably at least 8 amino acids, and even more preferably at least 15 amino acids from a polypeptide encoded by the nucleic acid sequence.

"Biological activity" as used herein, refers to all inherent biological properties of PIVKA-II. Such properties include, for example, the ability to bind to the antibodies described herein.

"Functional equivalent" as used herein, refers to a protein (e.g., an antibody) having the same characteristics (e.g., binding affinity) of the antibodies of the present invention.

The term "polypeptide" as used herein, refers to any polymeric chain of amino acids. The terms "peptide" and "protein" are used interchangeably with the term polypeptide and also refer to a polymeric chain of amino acids. The term "polypeptide" encompasses native or artificial proteins, protein fragments and polypeptide analogs of a protein sequence. A polypeptide may be monomeric or polymeric.

The term "isolated protein" or "isolated polypeptide" is a protein or polypeptide that by virtue of its origin or source of derivation is not associated with naturally associated components that accompany it in its native state; is substantially free of other proteins from the same species; is expressed by a cell from a different species; or does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

The term "recovering" as used herein, refers to the process of rendering a chemical species such as a polypeptide substantially free of naturally associated components by isolation, e.g., using protein purification techniques well known in the art.

The terms "specific binding" or "specifically binding", as used herein, in reference to the interaction of an antibody, a protein, or a peptide with a second chemical species, mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

The term "antibody", as used herein, broadly refers to any immunoglobulin (Ig) molecule comprised of four polypeptide chains, two heavy (H) chains and two light (L) chains, or any functional fragment, mutant, variant, or derivation thereof, which retains the essential epitope binding features of an Ig molecule. Such mutant, variant, or derivative antibody formats are known in the art. Nonlimiting embodiments of which are discussed below.

In a full-length antibody, each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgG, IgE, IgM, IgD, IgA and IgY), class (e.g., IgG 1, IgG2, IgG3, IgG4, IgA1 and IgA2) or subclass.

The term "antigen-binding portion" of an antibody (or simply "antibody portion"), as used herein, refers to one or more fragments of an antibody that retain the ability to specifically bind to an antigen (e.g., one or more epitopes of PIVKA-II). It has been shown that the antigen-binding function of an antibody can be performed by one or more fragments of a full-length antibody. Such antibody embodiments may also be bispecific, dual specific, or multi-specific, specifically binding to two or more different antigens. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546, Winter et al., International Appln. Publication No. WO 90/05144 A1 herein incorporated by reference), which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also encompassed within the term "antigen-binding portion" of an antibody. Other forms of single chain antibodies, such as diabodies, are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123). Such antibody binding portions are known in the art (Kontermann and Dubel eds., *Antibody Engineering* (2001) Springer-Verlag. New York. 790 pp. (ISBN 3-540-41354-5). The term "antibody construct" as used herein refers to a polypeptide comprising one or more the antigen binding portions of the invention linked to a linker polypeptide or an immunoglobulin constant domain. Linker polypeptides comprise two or more amino acid residues joined by peptide bonds and are used to link one or more antigen binding portions. Such linker polypeptides are well known in the art (see e.g., Holliger, P., et al. (1993) *Proc. Natl. Acad. Sci. USA* 90:6444-6448; Poljak, R. J., et al. (1994) *Structure* 2:1121-1123). An immunoglobulin constant domain refers to a heavy or light chain constant domain. Human IgG heavy chain and light chain constant domain amino acid sequences are known in the art.

Still further, an antibody or antigen-binding portion thereof may be part of a larger immunoadhesion molecule, formed by covalent or noncovalent association of the antibody or antibody portion with one or more other proteins or peptides. Examples of such immunoadhesion molecules include use of the streptavidin core region to make a tetrameric scFv molecule (Kipriyanov, S. M., et al. (1995) *Human Antibodies and Hybridomas* 6:93-101) and use of a cysteine residue, a marker peptide and a C-terminal polyhistidine tag to make bivalent and biotinylated scFv molecules (Kipriyanov, S. M., et al. (1994) *Mol. Immunol.* 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

An "isolated antibody", as used herein, is intended to refer to an antibody that is substantially free of other antibodies having different antigenic specificities (e.g., an isolated antibody that specifically binds at least one epitope of PIVKA-II with which the antibodies of the present invention are reactive and is substantially free of antibodies that specifically bind antigens or epitopes other than those present within PIVKA-II.

The terms "Kabat numbering", "Kabat definitions and "Kabat labeling" are used interchangeably herein. These terms, which are recognized in the art, refer to a system of numbering amino acid residues which are more variable (i.e. hypervariable) than other amino acid residues in the heavy and light chain variable regions of an antibody, or an antigen binding portion thereof (Kabat et al. (1971) *Ann. NY Acad, Sci.* 190:382-391 and Kabat, E. A., et al. (1991) *Sequences of Proteins of Immunological Interest, Fifth Edition*, U.S. Department of Health and Human Services, NIH Publication No. 91-3242).

As used herein, the term "CDR" refers to the complementarity determining region within antibody variable sequences. There are three CDRs in each of the variable regions of the heavy chain and the light chain, which are designated CDR1, CDR2 and CDR3, for each of the variable regions. The term "CDR set" as used herein refers to a group of three CDRs that occur in a single variable region capable of binding the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Chothia and coworkers (Chothia & Lesk, *J. Mol. Biol.* 196:901-917 (1987) and Chothia et al., *Nature* 342:877-883 (1989)) found that certain sub-portions within Kabat CDRs adopt nearly identical peptide backbone conformations, despite having great diversity at the level of amino acid sequence. These sub-portions were designated as L1, L2 and L3 or H1, H2 and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan (*FASEB J.* 9:133-139 (1995)) and MacCallum (*J Mol Biol* 262(5):732-45 (1996)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although preferred embodiments use Kabat or Chothia defined CDRs.

As used herein, the term "canonical" residue refers to a residue in a CDR or framework that defines a particular canonical CDR structure as defined by Chothia et al. (*J. Mol. Biol.* 196:901-907 (1987); Chothia et al., *J. Mol. Biol.* 227:799 (1992), both are incorporated herein by reference). According to Chothia et al., critical portions of the CDRs of many antibodies have nearly identical peptide backbone conformations despite great diversity at the level of amino acid sequence. Each canonical structure specifies primarily a set of peptide backbone torsion angles for a contiguous segment of amino acid residues forming a loop.

As used herein, the term "key" residues refer to certain residues within the variable region that have more impact on the binding specificity and/or affinity of an antibody, in particular a humanized antibody. A key residue includes, but is not limited to, one or more of the following: a residue that is adjacent to a CDR, a potential glycosylation site (can be either N- or O-glycosylation site), a rare residue, a residue capable of interacting with the antigen, a residue capable of interacting with a CDR, a canonical residue, a contact residue between heavy chain variable region and light chain variable region, a residue within the Vernier zone, and a residue in the region that overlaps between the Chothia definition of a variable heavy chain CDR1 and the Kabat definition of the first heavy chain framework.

As used herein, "Vernier" zone refers to a subset of framework residues that may adjust CDR structure and fine-tune the fit to antigen as described by Foote and Winter (1992, *J. Mol. Biol.* 224:487-499, which is incorporated herein by reference). Vernier zone residues form a layer underlying the CDRs and may impact on the structure of CDRs and the affinity of the antibody.

The term "activity" includes activities such as the binding specificity/affinity of an antibody for an antigen, for example, the antigen or antigens which the antibodies of the present invention are reactive.

The term "epitope" includes any polypeptide determinant capable of specific binding to an immunoglobulin or T-cell receptor. In certain embodiments, epitope determinants include chemically active surface groupings of molecules such as amino acids, sugar side chains, phosphoryl, or sulfonyl and, in certain embodiments, may have specific three-dimensional structural characteristics, and/or specific charge characteristics. An epitope is a region of an antigen that is bound by an antibody. In certain embodiments, an antibody is said to specifically bind an antigen when it preferentially recognizes its target antigen in a complex mixture of proteins and/or macromolecules.

The term "surface plasmon resonance", as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Jönsson, U., et al. (1993) *Ann. Biol. Clin.* 51:19-26; Jönsson, U., et al. (1991) *Biotechniques* 11:620-627; Johnsson, B., et al. (1995) *J. Mol. Recognit.* 8:125-131; and Johnnson, B., et al. (1991) *Anal. Biochem.* 198:268-277.

The term "$K_{on}$", as used herein, is intended to refer to the on rate constant for association of an antibody to the antigen to form the antibody/antigen complex as is known in the art.

The term "$K_{off}$", as used herein, is intended to refer to the off rate constant for dissociation of an antibody from the antibody/antigen complex as is known in the art.

The term "$K_d$", as used herein, is intended to refer to the dissociation constant of a particular antibody-antigen interaction as is known in the art.

The term "labeled binding protein" as used herein, refers to a protein with a label incorporated that provides for the identification of the binding protein. Preferably, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). Examples of labels for polypeptides include, but are not limited to, the following: radioisotopes or radionuclides (e.g., $^3$H, $^{14}$C, $^{35}$S, $^{90}$Y, $^{99}$Tc, $^{111}$In, $^{125}$I, $^{131}$I, $^{177}$Lu, $^{166}$Ho, or $^{153}$Sm); fluorescent labels (e.g., FITC, rhodamine, lanthanide phosphors), enzymatic labels (e.g., horseradish peroxidase, luciferase, alkaline phosphatase); chemiluminescent markers; biotinyl groups; predetermined polypeptide epitopes recognized by a secondary reporter (e.g., leucine zipper pair sequences, binding sites for secondary antibodies, metal binding domains, epitope tags); and magnetic agents, such as gadolinium chelates.

The term "antibody conjugate" refers to a binding protein, such as an antibody, chemically linked to a second chemical moiety, such as a therapeutic or cytotoxic agent. The term "agent" is used herein to denote a chemical compound, a mixture of chemical compounds, a biological macromolecule, or an extract made from biological materials. Preferably the therapeutic or cytotoxic agents include, but are not limited to, pertussis toxin, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

The terms "crystal", and "crystallized" as used herein, refer to an antibody, or antigen-binding portion thereof, that exists in the form of a crystal. Crystals are one form of the solid state of matter, which is distinct from other forms such as the amorphous solid state or the liquid crystalline state. Crystals are composed of regular, repeating, three-dimensional arrays of atoms, ions, molecules (e.g., proteins such as antibodies), or molecular assemblies (e.g., antigen/antibody complexes). These three-dimensional arrays are arranged according to specific mathematical relationships that are well-understood in the field. The fundamental unit, or building block, that is repeated in a crystal is called the asymmetric unit. Repetition of the asymmetric unit in an arrangement that conforms to a given, well-defined crystallographic symmetry provides the "unit cell" of the crystal. Repetition of the unit cell by regular translations in all three dimensions provides the crystal. See Giege, R. and Ducruix, A. Barrett, Crystallization of Nucleic Acids and Proteins, a Practical Approach, 2nd ed., pp. 20 1-16, Oxford University Press, New York, N.Y., (1999).

The term "polynucleotide" as referred to herein means a polymeric form of two or more nucleotides, either ribonucleotides or deoxynucleotides or a modified form of either type of nucleotide. The term includes single and double stranded forms of DNA but preferably is double-stranded DNA.

The term "isolated polynucleotide" as used herein shall mean a polynucleotide (e.g., of genomic, cDNA, or synthetic origin, or some combination thereof) that, by virtue of its origin, is not associated with all or a portion of a polynucleotide with which the "isolated polynucleotide" is found in nature; is operably linked to a polynucleotide that it is not linked to in nature; or does not occur in nature as part of a larger sequence.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences. "Operably linked" sequences include both expression control sequences that are contiguous with the gene of interest and expression control sequences that act in trans or at a distance to control the gene of interest. The term "expression control sequence" as used herein refers to polynucleotide sequences that are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include components whose presence is essential for expression and processing, and can also include additional components whose presence is advantageous, for example, leader sequences and fusion partner sequences.

"Transformation", as defined herein, refers to any process by which exogenous DNA enters a host cell. Transformation may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells that transiently express the inserted DNA or RNA for limited periods of time.

The term "recombinant host cell" (or simply "host cell"), as used herein, is intended to refer to a cell into which exogenous DNA has been introduced. It should be understood that such terms are intended to refer not only to the particular subject cell but also to the progeny of such a cell. Because certain modifications may occur in succeeding generations due to either mutation or environmental influences, such progeny may not, in fact, be identical to the parent cell, but are still included within the scope of the term "host cell" as used herein. Preferably, host cells include prokaryotic and eukaryotic cells selected from any of the Kingdoms of life. Preferred eukaryotic cells include protist, fungal, plant and animal cells. Most preferably, host cells include but are not limited to the prokaryotic cell line *E. coli*; mammalian cell lines CHO, HEK 293 and COS; the insect cell line Sf9; and the fungal cell *Saccharomyces cerevisiae*.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)), which is incorporated herein by reference for any purpose.

"Transgenic organism", as known in the art and as used herein, refers to an organism having cells that contain a transgene, wherein the transgene introduced into the organism (or an ancestor of the organism) expresses a polypeptide not naturally expressed in the organism. A "transgene" is a DNA construct, which is stably and operably integrated into the genome of a cell from which a transgenic organism develops, directing the expression of an encoded gene product in one or more cell types or tissues of the transgenic organism.

The term "regulate" and "modulate" are used interchangeably, and, as used herein, refers to a change or an alteration in the activity of a molecule of interest Modulation may be an increase or a decrease in the magnitude of a certain activity or function of the molecule of interest. Exemplary activities and functions of a molecule include, but are not limited to, binding characteristics, enzymatic activity, cell receptor activation, and signal transduction.

Correspondingly, the term "modulator," as used herein, is a compound capable of changing or altering an activity or function of a molecule of interest. For example, a modulator may cause an increase or decrease in the magnitude of a certain activity or function of a molecule compared to the magnitude of the activity or function observed in the absence of the modulator. In certain embodiments, a modulator is an inhibitor, which decreases the magnitude of at least one activity or function of a molecule. Exemplary inhibitors include, but are not limited to, proteins, peptides, antibodies, peptibodies, carbohydrates or small organic molecules. Peptibodies are described, e.g., in International Application Publication No. WO 01/83525.

The term "agonist", as used herein, refers to a modulator that, when contacted with a molecule of interest, causes an increase in the magnitude of a certain activity or function of the molecule compared to the magnitude of the activity or function observed in the absence of the agonist.

The term "antagonist" or "inhibitor", as used herein, refer to a modulator that, when contacted with a molecule of interest causes a decrease in the magnitude of a certain activity or function of the molecule compared to the magnitude of the activity or function observed in the absence of the antagonist.

As used herein, the term "effective amount" refers to the amount of a therapy which is sufficient to reduce or ameliorate the severity and/or duration of a disorder or one or more symptoms thereof, prevent the advancement of a disorder, cause regression of a disorder, prevent the recurrence, development, onset or progression of one or more symptoms associated with a disorder, detect a disorder, or enhance or improve the prophylactic or therapeutic effect(s) of another therapy (e.g., prophylactic or therapeutic agent).

The term "sample", as used herein, is used in its broadest sense. A "biological sample", as used herein, includes, but is not limited to, any quantity of a substance from a living thing or formerly living thing. Such living things include, but are not limited to, humans, mice, rats, monkeys, dogs, rabbits and other mammalian or non-mammalian animals. Such substances include, but are not limited to, blood, serum, urine, synovial fluid, cells, organs, tissues (e.g., brain), bone marrow, lymph nodes, cerebrospinal fluid, and spleen.

Unless otherwise defined herein, scientific and technical terms used in connection with the present invention shall have the meanings that are commonly understood by those of ordinary skill in the art. The meaning and scope of the terms should be clear; however, in the event of any latent ambiguity, definitions provided herein take precedent over any dictionary or extrinsic definition. Further, unless otherwise required by context, singular terms shall include pluralities and plural terms shall include the singular. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise.

Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

According to the invention and, in particular, for the purpose of assessing the binding affinities of the antibodies of the present invention, a process may be used as described in International Application Publication No. WO 2004/067561, which is incorporated herein by reference. Said process comprises unfolding a natural, recombinant or synthetic peptide or a derivative thereof; exposing the at least partially unfolded peptide or derivative thereof to a detergent, reducing the detergent action and continuing incubation.

For the purpose of unfolding the peptide, hydrogen bond-breaking agents such as, for example, hexafluoroisopropanol (HFIP) may be allowed to act on the protein. Times of action of a few minutes, for example about 10 to 60 minutes, are sufficient when the temperature of action is from about 20 to 50° C. and in particular about 35 to 40° C. Subsequent dissolution of the residue evaporated to dryness, preferably in concentrated form, in suitable organic solvents miscible with aqueous buffers, such as, for example, dimethyl sulfoxide (DMSO), results in a suspension of the at least partially unfolded peptide or derivative thereof, which can be used subsequently. If required, the stock suspension may be stored at low temperature, for example at about −20° C., for an interim period.

Alternatively, the peptide or the derivative thereof may be taken up in slightly acidic, preferably aqueous, solution, for example, an about 10 mM aqueous HCl solution. After an incubation time of usually a few minutes, insoluble components are removed by centrifugation. A few minutes at 10000 g is expedient. These method steps are preferably carried out at room temperature, i.e. a temperature in the range from 20 to 30° C. The supernatant obtained after centrifugation contains the peptide or the derivative thereof and may be stored at low temperature, for example at about −20° C., for an interim period.

A. Preparation of Monoclonal Antibodies

Monoclonal antibodies can be prepared using a wide variety of techniques known in the art including the use of hybridoma, recombinant, and phage display technologies, or a combination thereof. For example, it is preferred that monoclonal antibodies of the present invention be produced using hybridoma techniques including those known in the art and taught, for example, in Harlow et al., Antibodies: A Laboratory Manual (Cold Spring Harbor Laboratory Press, 2nd ed. 1988); Hammerling, et al., in: Monoclonal Antibodies and T-Cell Hybridomas 563-681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. In one embodiment, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention. Briefly, mice can be immunized with the antigen of interest. In a preferred embodiment, the antigen is administered with an adjuvant to stimulate the immune response. Such adjuvants include complete or incomplete Freund's adjuvant, RIBI (muramyl dipeptides) or ISCOM (immunostimulating complexes). Such adjuvants may protect the polypeptide from rapid dispersal by sequestering it in a local deposit, or they may contain substances that stimulate the host to secrete factors that are chemotactic for macrophages and other components of the immune system. Preferably, if a polypeptide is being administered, the immunization schedule will involve two or more administrations of the polypeptide, spread out over several weeks.

After immunization of an animal with the antigen, antibodies and/or antibody-producing cells may be obtained from the animal. An antibody-containing serum is obtained from the animal by bleeding or sacrificing the animal. The serum may be used as it is obtained from the animal, an immunoglobulin fraction may be obtained from the serum, or the antibodies may be purified from the serum. Serum or immunoglobulins obtained in this manner are polyclonal, thus having a heterogeneous array of properties.

Once an immune response is detected, e.g., antibodies specific for the antigen are detected in the mouse serum, the mouse spleen is harvested and splenocytes isolated. The splenocytes are then fused by well-known techniques to any suitable myeloma cells, for example cells from cell line SP20 available from the American Type Culture Collection (Manassas, Va.). Hybridomas are selected and cloned by limited dilution. The hybridoma clones are then assayed by methods known in the art for cells that secrete antibodies capable of binding to the peptide or antigen of interest. Ascites fluid, which generally contains high levels of antibodies, can be generated by immunizing mice with positive hybridoma clones.

In another embodiment, antibody-producing immortalized hybridomas may be prepared from the immunized animal. After immunization, the animal is sacrificed and the splenic B cells are fused to immortalized myeloma cells as is well known in the art. See, e.g., Harlow and Lane, supra. In a preferred embodiment, the myeloma cells do not secrete immunoglobulin polypeptides (a non-secretory cell line). After fusion and antibiotic selection, the hybridomas are screened using the antigen, or a portion thereof, or a cell expressing the antigen. In a preferred embodiment, the initial screening is performed using an enzyme-linked immunoassay (ELISA) or a radioimmunoassay (RIA), preferably an ELISA. An example of ELISA screening is provided in International Application Publication No. WO 00/37504, herein incorporated by reference.

Antibody-producing hybridomas are selected, cloned and further screened for desirable characteristics, including robust hybridoma growth, high antibody production and desirable antibody characteristics, as discussed further below. Hybridomas may be cultured and expanded in vivo in syngeneic animals, in animals that lack an immune system, e.g., nude mice, or in cell culture in vitro. Methods of selecting, cloning and expanding hybridomas are well known to those of ordinary skill in the art.

In a preferred embodiment, the hybridomas are mouse hybridomas, as described above. In another preferred embodiment, the hybridomas are produced in a non-human, non-mouse species such as rats, sheep, pigs, goats, cattle or horses. In another embodiment, the hybridomas are human hybridomas, in which a human non-secretory myeloma is fused with a human cell expressing the antibody.

B. Other Methods of Production of the Antibodies of the Present Invention

As noted above, antibodies of the present invention may be produced by any of a number of techniques known in the art. For example, the antibody may be produced based upon expression from host cells, wherein expression vector(s) encoding the heavy and light chains is (are) transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although, it is possible to express the antibodies of the invention in either prokaryotic or eukaryotic host cells, expression of antibodies in eukaryotic cells is preferable, and most preferable in mammalian host cells, because such eukaryotic cells (and in particular mammalian cells) are more likely than prokaryotic cells to assemble and secrete a properly folded and immunologically active antibody.

Preferred mammalian host cells for expressing the recombinant antibodies of the invention include Chinese Hamster Ovary (CHO cells) (including dhfr- CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *Mol. Biol.* 159:601-621), NS0 myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce functional antibody fragments, such as Fab fragments or scFv molecules. It will be understood that variations on the above procedure are within the scope of the present invention. For example, it may be desirable to transfect a host cell with DNA encoding functional fragments of either the light chain and/or the heavy chain of an antibody of this invention. Recombinant DNA technology may also be used to remove some, or all, of the DNA encoding either or both of the light and heavy chains that is not necessary for binding to the antigens of interest. The molecules expressed from such truncated DNA molecules are also encompassed by the antibodies of the invention. In addition, bifunctional antibodies may be produced in which one heavy and one light chain are an antibody of the invention and the other heavy and light chain are specific for an antigen other than the antigens of interest by crosslinking an antibody of the invention to a second antibody by standard chemical crosslinking methods.

In a preferred system for recombinant expression of an antibody, or antigen-binding portion thereof, of the invention, a recombinant expression vector encoding both the antibody heavy chain and the antibody light chain is introduced into dhfr- CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium. Still further the invention provides a method of synthesizing a recombinant antibody of the invention by culturing a host cell of the invention in a suitable culture medium until a recombinant antibody of the invention is synthesized. The method can further comprise isolating the recombinant antibody from the culture medium.

C. Preparation of Antibodies for Diagnostic and Other Applications

As noted above, preferably, antibodies of the present invention exhibit a high binding affinity to one or more epitopes of PIVKA-II, e.g., as assessed by any one of several in vitro and in vivo assays known in the art (e.g., see examples below).

In certain embodiments, the antibody comprises a heavy chain constant region, such as an IgG1, IgG2, IgG3, IgG4, IgA, IgE, IgM or IgD constant region. Preferably, the heavy chain constant region is an IgG1 heavy chain constant region or an IgG4 heavy chain constant region. Furthermore, the antibody can comprise a light chain constant region, either a kappa light chain constant region or a lambda light chain constant region. Preferably, the antibody comprises a kappa light chain constant region. Alternatively, the antibody portion can be, for example, a Fab fragment or a single chain Fv fragment.

Replacements of amino acid residues in the Fc portion to alter antibody effector function are known in the art (Winter, et al. U.S. Pat. Nos. 5,648,260 and 5,624,821). The Fc portion of an antibody mediates several important effector functions e.g. cytokine induction, ADCC, phagocytosis, complement dependent cytotoxicity (CDC) and half-life/clearance rate of antibody and antigen-antibody complexes. In some cases, these effector functions are desirable for therapeutic antibody but in other cases might be unnecessary or even deleterious, depending on the therapeutic objectives. Certain human IgG isotypes, particularly IgG1 and IgG3, mediate ADCC and CDC via binding to FcγRs and complement C1q, respectively. Neonatal Fc receptors (FcRn) are the critical components determining the circulating half-life of antibodies. In still another embodiment, at least one amino acid residue is replaced in the constant region of the antibody, for example the Fc region of the antibody, such that effector functions of the antibody are altered.

One embodiment provides a labeled binding protein wherein an antibody or antibody portion of the invention is derivatized or linked to another functional molecule (e.g., another peptide or protein). For example, a labeled binding protein of the invention can be derived by functionally linking an antibody or antibody portion of the invention (by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that can mediate associate of the antibody or antibody portion with another molecule (such as a streptavidin core region or a polyhistidine tag).

Useful detectable agents with which an antibody or antibody portion of the invention may be derivatized include fluorescent compounds. Exemplary fluorescent detectable agents include fluorescein, fluorescein isothiocyanate, rhodamine, 5-dimethylamine-1-napthalenesulfonyl chloride, phycoerythrin and the like. An antibody may also be derivatized with detectable enzymes, such as alkaline phosphatase, horseradish peroxidase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody may also be derivatized with biotin, and detected through indirect measurement of avidin or streptavidin binding.

Another embodiment of the invention provides a crystallized binding protein. Preferably, the invention relates to crystals of whole antibodies and fragments thereof as disclosed herein, and formulations and compositions comprising such crystals. In one embodiment the crystallized binding protein has a greater half-life in vivo than the soluble counterpart of the binding protein. In another embodiment, the binding protein retains biological activity after crystallization.

Crystallized binding protein of the invention may be produced according methods known in the art and as disclosed in International Appln. Publication No. WO 02/072636, incorporated herein by reference.

Another embodiment of the invention provides a glycosylated binding protein wherein the antibody or antigen-binding portion thereof comprises one or more carbohydrate residues. Nascent in vivo protein production may undergo further processing, known as post-translational modification. In particular, sugar (glycosyl) residues may be added enzymatically, a process known as glycosylation. The resulting proteins bearing covalently linked oligosaccharide side chains are known as glycosylated proteins or glycoproteins. Antibodies are glycoproteins with one or more carbohydrate residues in the Fc domain, as well as the variable domain. Carbohydrate residues in the Fc domain have important effect on the effector function of the Fc domain, with minimal effect on antigen binding or half-life of the antibody (R. Jefferis, *Biotechnol. Prog.* 21 (2005), pp. 11-16). In contrast, glycosylation of the variable domain may have an effect on the antigen binding activity of the antibody. Glycosylation in the variable domain may have a negative effect on antibody binding affinity, likely due to steric hindrance (Co, M. S., et al., *Mol. Immunol.* (1993) 30:1361-1367), or result in increased affinity for the antigen (Wallick, S. C., et al., *Exp. Med.* (1988) 168:1099-1109; Wright, A., et al., *EMBO J.* (1991) 10:2717 2723).

One aspect of the present invention is directed to generating glycosylation site mutants in which the O- or N-linked glycosylation site of the binding protein has been mutated. One skilled in the art can generate such mutants using standard well-known technologies. The creation of glycosylation site mutants that retain the biological activity but have increased or decreased binding activity are another object of the present invention.

In still another embodiment, the glycosylation of the antibody or antigen-binding portion of the invention is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region glycosylation sites to thereby eliminate glycosylation at that site. Such aglycosylation may increase the affinity of the antibody for antigen. Such an approach is described in further detail in International Appln. Publication No. WO 03/016466A2, and U.S. Pat. Nos. 5,714,350 and 6,350,861, each of which is incorporated herein by reference in its entirety.

Additionally or alternatively, a modified antibody of the invention can be made that has an altered type of glycosylation, such as a hypofucosylated antibody having reduced amounts of fucosyl residues or an antibody having increased bisecting GlcNAc structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. See, for example, Shields, R. L. et al. (2002) *J. Biol. Chem.* 277:26733-26740; Umana et al. (1999) *Nat. Biotech.* 17:176-1, as well as, European Patent NO.: EP 1,176,195; International Appln. Publication Nos. WO 03/035835 and WO 99/54342 80, each of which is incorporated herein by reference in its entirety.

Protein glycosylation depends on the amino acid sequence of the protein of interest, as well as the host cell in which the protein is expressed. Different organisms may produce different glycosylation enzymes (e.g., glycosyltransferases and glycosidases), and have different substrates (nucleotide sugars) available. Due to such factors, protein glycosylation pattern, and composition of glycosyl residues, may differ depending on the host system in which the particular protein is expressed. Glycosyl residues useful in the invention may include, but are not limited to, glucose, galactose, mannose, fucose, n-acetylglucosamine and sialic acid. Preferably the glycosylated binding protein comprises glycosyl residues such that the glycosylation pattern is human.

It is known to those skilled in the art that differing protein glycosylation may result in differing protein characteristics. For instance, the efficacy of a therapeutic protein produced in a microorganism host, such as yeast, and glycosylated utilizing the yeast endogenous pathway may be reduced compared to that of the same protein expressed in a mammalian cell, such as a CHO cell line. Such glycoproteins may also be immunogenic in humans and show reduced half-life in vivo after administration. Specific receptors in humans and other animals may recognize specific glycosyl residues and promote the rapid clearance of the protein from the bloodstream. Other adverse effects may include changes in protein folding, solubility, susceptibility to proteases, trafficking, transport, compartmentalization, secretion, recognition by other proteins or factors, antigenicity, or allergenicity. Accordingly, a practitioner may prefer a therapeutic protein with a specific composition and pattern of glycosylation, for example glycosylation composition and pattern identical, or at least similar, to that produced in human cells or in the species-specific cells of the intended subject animal.

Expressing glycosylated proteins different from that of a host cell may be achieved by genetically modifying the host cell to express heterologous glycosylation enzymes. Using techniques known in the art a practitioner may generate antibodies or antigen-binding portions thereof exhibiting human protein glycosylation. For example, yeast strains have been genetically modified to express non-naturally occurring glycosylation enzymes such that glycosylated proteins (glycoproteins) produced in these yeast strains exhibit protein glycosylation identical to that of animal cells, especially human cells (U.S. Patent Application Publication Nos. 20040018590 and 20020137134 and International Appln. Publication No. WO 05/100584 A2).

The term "multivalent binding protein" is used in this specification to denote a binding protein comprising two or more antigen binding sites. The multivalent binding protein is preferably engineered to have the three or more antigen binding sites, and is generally not a naturally occurring antibody. The term "multispecific binding protein" refers to a binding protein capable of binding two or more related or unrelated targets. Dual variable domain (DVD) binding proteins as used herein, are binding proteins that comprise two or more antigen binding sites and are tetravalent or multivalent binding proteins. Such DVDs may be monospecific, i.e capable of binding one antigen or multispecific, i.e. capable of binding two or more antigens. DVD binding proteins comprising two heavy chain DVD polypeptides and two light chain DVD polypeptides are referred to a DVD Ig. Each half of a DVD Ig comprises a heavy chain DVD polypeptide, and a light chain DVD polypeptide, and two antigen binding sites. Each binding site comprises a heavy chain variable domain and a light chain variable domain with a total of 6 CDRs involved in antigen binding per antigen binding site. DVD binding proteins and methods of making DVD binding proteins are disclosed in U.S. patent application Ser. No. 11/507,050 and incorporated herein by reference.

One aspect of the invention pertains to a DVD binding protein comprising binding proteins capable of binding to one or more epitopes of PIVKA-II. Preferably, the DVD binding protein is capable of binding the epitope and a second target.

In addition to the binding proteins, the present invention is also directed to an anti-idiotypic (anti-Id) antibody specific for such binding proteins of the invention. An anti-Id antibody is an antibody, which recognizes unique determinants generally associated with the antigen-binding region of another antibody. The anti-Id can be prepared by immunizing an animal with the binding protein or a CDR containing region thereof. The immunized animal will recognize, and respond to the idiotypic determinants of the immunizing antibody and produce an anti-Id antibody. The anti-Id antibody may also be used as an "immunogen" to induce an immune response in yet another animal, producing a so-called anti-anti-Id antibody.

Further, it will be appreciated by one skilled in the art that a protein of interest may be expressed using a library of host cells genetically engineered to express various glycosylation enzymes, such that member host cells of the library produce the protein of interest with variant glycosylation patterns. A practitioner may then select and isolate the protein of interest with particular novel glycosylation patterns. Preferably, the protein having a particularly selected novel glycosylation pattern exhibits improved or altered biological properties.

D. Uses of the Antibodies

Given their ability to bind to PIVKA-II, or epitopes or portions thereof, the antibodies of the invention can be used to detect PIVKA-II in a biological sample (such as, for example, serum, blood, tissue or plasma), using a conventional competitive or non-competitive immunoassay (e.g., an enzyme linked immunosorbent assay (ELISA), a radioimmunoassay (RIA), immunometric, sandwich assay or tissue immunohistochemistry). Such detection may then result in a diagnosis of HCC or liver cancer for the patient from which the biological sample was obtained.

The invention therefore provides a method for detecting PIVKA-II in a biological sample comprising contacting a biological sample with an antibody, or antibody portion, of the present invention and detecting PIVKA-II or a portion (e.g., epitope thereof) by detecting formation of an antigen/antibody complex. The antibody may be directly or indirectly labeled with a detectable substance to facilitate detection of the bound or unbound antigen (i.e., PIVKA-II). Suitable detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{3}H$, $^{14}C$, $^{35}S$, $^{90}Y$, $^{99}Tc$, $^{111}In$, $^{125}I$, $^{131}I$, $^{177}Lu$, $^{166}Ho$, or $^{153}Sm$.

As an alternative to labeling the antibody, the antigen can be assayed in biological fluids by a competition immunoassay utilizing recombinant standards labeled with a detectable substance and an unlabeled antibody. In this assay, the biological sample, the labeled recombinant antigen standard and the antibody are combined, and the amount of labeled peptide standard bound to the unlabeled antibody is determined. The amount of antigen in the biological sample is inversely proportional to the amount of labeled antigen standard bound to the antibody.

To illustrate the above assays in connection with the present invention, in one embodiment of the present invention, antibody to PIVKA-II (or to epitopes or portions of full-length PIVKA-II), such as 3C10, is coated on a solid phase (or is present in a liquid phase). The test or biological sample (e.g., serum, plasma, urine, etc.) is then contacted with the solid phase. If PIVKA-II antigen is present in the sample, the antibody bound to the solid phase will bind to the PIVKA-II antigen which may then be detected by either a direct or indirect method. The direct method comprises simply detecting presence of the complex itself and thus presence of the PIVKA-II antigen. In the indirect method, a conjugate is added to the bound PIVKA-II antigen. The conjugate comprises a second antibody (usually different from the first antibody coated onto the solid phase), which binds to the bound PIVKA-II antigen, attached to a signal-generating compound or label. Should the second antibody bind to the bound antigen, the signal-generating compound generates a measurable signal. Such signal then indicates presence of the antigen in the test sample. It should be noted that the initial capture antibody (for detecting PIVKA-II antigens) used in the immunoassay may be covalently or non-covalently (e.g., ionic, hydrophobic, etc.) attached to the solid phase. Linking agents for covalent attachment are known in the art and may be part of the solid phase or derivatized to it prior to coating.

Examples of solid phases used in diagnostic immunoassays are porous and non-porous materials, latex particles, magnetic particles, microparticles (see U.S. Pat. No. 5,705,330), beads, membranes, microtiter wells and plastic tubes. The choice of solid phase material and method of labeling the antigen or antibody present in the conjugate, if desired, are determined based upon desired assay format performance characteristics.

As noted above, the conjugate (or indicator reagent) will comprise an antibody (or perhaps anti-antibody, depending upon the assay), attached to a signal-generating compound or label. This signal-generating compound or "label" is itself detectable or may be reacted with one or more additional compounds to generate a detectable product. Examples of signal-generating compounds include chromogens, radioisotopes (e.g., 125I, 131I, 32P, 3H, 35S and 14C), chemiluminescent compounds (e.g., acridinium), particles (visible or fluorescent), nucleic acids, complexing agents, or catalysts such as enzymes (e.g., alkaline phosphatase, acid phosphatase, horseradish peroxidase, beta-galactosidase and ribonuclease). In the case of enzyme use (e.g., alkaline phosphatase or horseradish peroxidase), addition of a chromo-, fluro-, or lumo-genic substrate results in generation of a detectable signal. Other detection systems such as time-resolved fluorescence, internal-reflection fluorescence, amplification (e.g., polymerase chain reaction) and Raman spectroscopy are also useful.

Examples of biological fluids which may be tested by the above immunoassays include plasma, urine, whole blood, dried whole blood, serum, cerebrospinal fluid, saliva, tears, nasal washes or aqueous extracts of tissues and cells.

Alternatively, in order to detect the presence of PIVKA-II in a biological sample, one may coat the solid phase with PIVKA-II antigen and then contact the solid phase with labeled antibody to PIVKA-II antigen, such as monoclonal antibody 3C10, for a time and under conditions sufficient to allow the immobilized antigen to bind to the labeled antibody. Subsequent thereto, the test sample may be added to the antigen-antibody complex. If PIVKA-II is present in the test sample, it will then bind to the bound labeled antibody. A detectable signal is then generated by the label indicating presence of the PIVKA-II antigen in the test sample.

Additionally, in an alternative assay format, one may use a PIVKA-II recombinant standard labeled with a detectable substance and an unlabeled antibody such as 3C10. In this assay, the biological test sample, the labeled recombinant PIVKA-II antigen standard and the 3C10 monoclonal antibody are combined, and the amount of labeled PIVKA-II standard bound to the unlabeled antibody is determined. The amount of PIVKA-II antigen in the biological sample is inversely proportional to the amount of labeled PIVKA-II antigen standard bound to the antibody.

Other assay formats which may be used for purposes of the present invention, in order to simultaneously detect antigens and antibodies include, for example, Dual assay strip blots, a rapid test, a Western blot, as well as the use of paramagnetic particles in, for example, an Architect® assay (Frank Quinn, The Immunoassay Handbook, Second edition, edited by David Wild, pages 363-367, 2001). Such formats are known to those of ordinary skill in the art.

It should also be noted that the elements of the assays described above are particularly suitable for use in the form of a kit. The kit may also comprise one container such as vial, bottles or strip, with each container with a pre-set solid phase, and other containers containing the respective conjugates.

These kits may also contain vials or containers of other reagents needed for performing the assay, such as washing, processing and indicator reagents.

Of course, any of the exemplary formats herein and any assay or kit according to the invention can be adapted or optimized for use in automated and semi-automated systems (including those in which there is a solid phase comprising a microparticle), as described, e.g., in U.S. Pat. Nos. 5,089,424 and 5,006,309, and as, e.g., commercially marketed by Abbott Laboratories (Abbott Park, Ill.) including but not limited to Abbott's ARCHITECT®, AxSYM, IMX, PRISM, and Quantum II platforms, as well as other platforms.

Additionally, the assays and kits of the present invention optionally can be adapted or optimized for point of care assay systems, including Abbott's Point of Care (i-STAT™) electrochemical immunoassay system. Immunosensors and methods of manufacturing and operating them in single-use test devices are described, for example in U.S. Pat. No. 5,063,081 and published U.S. Patent Application Nos. 20030170881, 20040018577, 20050054078, and 20060160164 (incorporated by reference herein for their teachings regarding same).

Further, it has been noted that PIVKA-II may induce malignancy of a tumor (Shiraha, *J. Biol. Chem.* Feb. 25, 2005; 280(8):6409-15). Thus, the present invention also provides methods for reducing PIVKA-II activity, in a human suffering from a disease or disorder with which PIVKA-II activity is associated (e.g., liver cancer or HCC). This method comprises administering to the subject an antibody (i.e., 3C10) or portion thereof (e.g., Fab' fragment) of the invention such that PIVKA-II activity in the subject is reduced (i.e., passive immunization). Moreover, an antibody of the invention (or fragment thereof) can be administered to a non-human mammal for therapeutic purposes, other veterinary purposes or for study of the effect of the antibody in an animal having a condition mimicking that found in humans. In particular, such animal models may be useful for evaluating the therapeutic efficacy of antibodies of the invention (e.g., testing of dosages and time courses of administration).

Non-limiting examples of disorders that can be treated with the antibodies of the invention include those disorders discussed in the section below pertaining to pharmaceutical compositions of the antibodies of the invention.

D. Pharmaceutical Compositions

As noted above, the invention also provides pharmaceutical compositions comprising an antibody, or antigen-binding portion thereof, of the invention and a pharmaceutically acceptable carrier. The pharmaceutical compositions comprising antibodies of the invention are for use in, but not limited to, diagnosing, detecting, or monitoring a disorder, in preventing, treating, managing, or ameliorating of a disorder or one or more symptoms thereof, and/or in research. In a specific embodiment, a composition comprises one or more antibodies of the invention. In another embodiment, the pharmaceutical composition comprises one or more antibodies of the invention and one or more prophylactic or therapeutic agents other than antibodies of the invention for treating a disorder in which PIVKA-II activity is detrimental. Preferably, the prophylactic or therapeutic agents known to be useful for or having been or currently being used in the prevention, treatment, management, or amelioration of a disorder or one or more symptoms thereof. In accordance with these embodiments, the composition may further comprise of a carrier, diluent or excipient.

The antibodies and antibody-portions of the invention can be incorporated into pharmaceutical compositions suitable for administration to a subject. Typically, the pharmaceutical composition comprises an antibody or antibody portion of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody or antibody portion.

Various delivery systems are known and can be used to administer one or more antibodies of the invention or the combination of one or more antibodies of the invention and a prophylactic agent or therapeutic agent useful for preventing, managing, treating, or ameliorating a disorder or one or more symptoms thereof, e.g., encapsulation in liposomes, microparticles, microcapsules, recombinant cells capable of expressing the antibody or antibody fragment, receptor-mediated endocytosis (see, e.g., Wu and Wu, *J. Biol. Chem.* 262:4429-4432 (1987)), construction of a nucleic acid as part of a retroviral or other vector, etc. Methods of administering a prophylactic or therapeutic agent of the invention include, but are not limited to, parenteral administration (e.g., intradermal, intramuscular, intraperitoneal, intravenous and subcutaneous), epidural administration, intratumoral administration, and mucosal adminsitration (e.g., intranasal and oral routes). In addition, pulmonary administration can be employed, e.g., by use of an inhaler or nebulizer, and formulation with an aerosolizing agent. See, e.g., U.S. Pat. Nos. 6,019,968, 5,985,320, 5,985,309, 5,934, 272, 5,874,064, 5,855,913, 5,290,540, and 4,880,078; and International Appln. Publication Nos. WO 92/19244, WO 97/32572, WO 97/44013, WO 98/31346, and WO 99/66903, each of which is incorporated herein by reference their entireties. In one embodiment, an antibody of the invention, combination therapy, or a composition of the invention is administered using Alkermes AIR® pulmonary drug delivery technology (Alkermes, Inc., Cambridge, Mass.). In a specific embodiment, prophylactic or therapeutic agents of the invention are administered intramuscularly, intravenously, intratumorally, orally, intranasally, pulmonary, or subcutaneously. The prophylactic or therapeutic agents may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In a specific embodiment, it may be desirable to administer the prophylactic or therapeutic agents of the invention locally to the area in need of treatment; this may be achieved by, for example, and not by way of limitation, local infusion, by injection, or by means of an implant, said implant being of a porous or non-porous material, including membranes and matrices, such as sialastic membranes, polymers, fibrous matrices (e.g., Tissuel®), or collagen matrices. In one embodiment, an effective amount of one or more antibodies of the invention antagonists is administered locally to the affected area to a subject to prevent, treat, manage, and/or ameliorate a disorder or a symptom thereof. In another embodiment, an effective amount of one or more antibodies of the invention is administered locally to the affected area in combination with an effective amount of one or more therapies (e.g., one or more prophylactic or therapeutic agents) other than an antibody of the invention of a subject to prevent, treat, manage, and/or ameliorate a disorder or one or more symptoms thereof.

In another embodiment, the prophylactic or therapeutic agent can be delivered in a controlled release or sustained release system. In one embodiment, a pump may be used to achieve controlled or sustained release (see Langer, supra; Sefton, 1987, *CRC Crit. Ref. Biomed. Eng.* 14:20; Buchwald et al., 1980, *Surgery* 88:507; Saudek et al., 1989, *N. Engl. J. Med.* 321:574). In another embodiment, polymeric materials can be used to achieve controlled or sustained release of the therapies of the invention (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, *J. Macromol. Sci. Rev. Macromol. Chem.* 23:61; see also Levy et al., 1985, *Science* 228:190; During et al., 1989, *Ann. Neurol.* 25:351; Howard et al., 1989, *J. Neurosurg.* 7 1:105); U.S. Pat. No. 5,679,377; U.S. Pat. No. 5,916,597; U.S. Pat. No. 5,912,015; U.S. Pat. No. 5,989,463; U.S. Pat. No. 5,128,326; International Appln. Publication No. WO 99/15154; and International Appln. Publication No. WO 99/20253. Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In a preferred embodiment, the polymer used in a sustained release formulation is inert, free of leachable impurities, stable on storage, sterile, and biodegradable. In yet another embodiment, a controlled or sustained release system can be placed in proximity of the prophylactic or therapeutic target, thus requiring only a fraction of the systemic dose (see, e.g., Goodson, in Medical Applications of Controlled Release, supra, vol. 2, pp. 115-138 (1984)).

Controlled release systems are discussed in the review by Langer (1990, *Science* 249:1527-1533). Any technique known to one of skill in the art can be used to produce sustained release formulations comprising one or more therapeutic agents of the invention. See, e.g., U.S. Pat. No. 4,526,938, International Appln. Publication No. WO 91/05548, International Appln. Publication No. WO 96/20698, Ning et al., 1996, "Intratumoral Radioimmunotheraphy of a Human Colon Cancer Xenograft Using a Sustained-Release Gel," *Radiotherapy & Oncology* 39:179-189, Song et al., 1995, "Antibody Mediated Lung Targeting of Long-Circulating Emulsions," *PDA Journal of Pharmaceutical Science & Technology* 50:372-397, Cleek et al., 1997, "Biodegradable Polymeric Carriers for a bFGF Antibody for Cardiovascular Application," Pro. Int'l. Symp. Control. Rel. Bioact. Mater. 24:853-854, and Lam et al., 1997, "Microencapsulation of Recombinant Humanized Monoclonal Antibody for Local Delivery," Proc. Int'l. Symp. Control Rel. Bioact. Mater. 24:759-760, each of which is incorporated herein by reference in their entireties.

In a specific embodiment, where the composition of the invention is a nucleic acid encoding a prophylactic or therapeutic agent, the nucleic acid (encoded an antibody of the invention) can be administered in vivo to promote expression of its encoded prophylactic or therapeutic agent, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see, e.g., Joliot et al., 1991, *Proc. Natl. Acad. Sci. USA* 88:1864-1868). Alternatively, a nucleic acid can be introduced intracellularly and incorporated within host cell DNA for expression by homologous recombination.

A pharmaceutical composition of the invention is formulated to be compatible with its intended route of administration. Examples of routes of administration include, but are not limited to, parenteral, e.g., intravenous, intradermal, subcutaneous, oral, intranasal (e.g., inhalation), transdermal (e.g., topical), transmucosal, and rectal administration. In a specific embodiment, the composition is formulated in accordance with routine procedures as a pharmaceutical composition adapted for intravenous, subcutaneous, intramuscular, oral, intranasal, or topical administration to human beings. Typically, compositions for intravenous administration are solutions in sterile isotonic aqueous buffer. Where necessary, the composition may also include a solubilizing agent and a local anesthetic such as lidocaine to ease pain at the site of the injection.

If the compositions of the invention are to be administered topically, the compositions can be formulated in the form of an ointment, cream, transdermal patch, lotion, gel, shampoo, spray, aerosol, solution, emulsion, or other form well known to one of skill in the art. See, e.g., Remington's Pharmaceutical Sciences and Introduction to Pharmaceutical Dosage Forms, 19th ed., Mack Pub. Co., Easton, Pa. (1995). For non-sprayable topical dosage forms, viscous to semi-solid or solid forms comprising a carrier or one or more excipients compatible with topical application and having a dynamic viscosity preferably greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, preferably in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms if desired. Examples of such additional ingredients are well known in the art.

If the method of the invention comprises intranasal administration of a composition, the composition can be formulated in an aerosol form, spray, mist or in the form of drops. In particular, prophylactic or therapeutic agents for use according to the present invention can be conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In the case of a pressurized aerosol, the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

If the method of the invention comprises oral administration, compositions can be formulated orally in the form of tablets, capsules, cachets, gelcaps, solutions, suspensions, and the like. Tablets or capsules can be prepared by conventional means with pharmaceutically acceptable excipients such as binding agents (e.g., pregelatinised maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulphate). The tablets may be coated by methods well-known in the art. Liquid preparations for oral administration may take the form of, but not limited to, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate. Preparations for oral administration may be suitably formulated for slow release, controlled release, or sustained release of a prophylactic or therapeutic agent(s).

The method of the invention may comprise pulmonary administration, e.g., by use of an inhaler or nebulizer, of a composition formulated with an aerosolizing agent. See, e.g., U.S. Pat. Nos. 6,019,968, 5,985,320, 5,985,309, 5,934,272, 5,874,064, 5,855,913, 5,290,540, and 4,880,078; and International Appln. Publication Nos. WO 92/19244, WO 97/32572, WO 97/44013, WO 98/31346, and WO 99/66903, each of which is incorporated herein by reference their entireties. In a specific embodiment, an antibody of the invention, combination therapy, and/or composition of the invention is administered using Alkermes AIR® pulmonary drug delivery technology (Alkermes, Inc., Cambridge, Mass.).

The method of the invention may comprise administration of a composition formulated for parenteral administration by injection (e.g., by bolus injection or continuous infusion). Formulations for injection may be presented in unit dosage form (e.g., in ampoules or in multi-dose containers) with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle (e.g., sterile pyrogen-free water) before use. The methods of the invention may additionally comprise of administration of compositions formulated as depot preparations. Such long acting formulations may be administered by implantation (e.g., subcutaneously or intramuscularly) or by intramuscular injection. Thus, for example, the compositions may be formulated with suitable polymeric or hydrophobic materials (e.g., as an emulsion in an acceptable oil) or ion exchange resins, or as sparingly soluble derivatives (e.g., as a sparingly soluble salt).

The methods of the invention encompass administration of compositions formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Generally, the ingredients of compositions are supplied either separately or mixed together in unit dosage form, for example, as a dry lyophilized powder or water free concentrate in a hermetically sealed container such as an ampoule or sachette indicating the quantity of active agent. Where the mode of administration is infusion, composition can be dispensed with an infusion bottle containing sterile pharmaceutical grade water or saline. Where the mode of administration is by injection, an ampoule of sterile water for injection or saline can be provided so that the ingredients may be mixed prior to administration.

In particular, the invention also provides that one or more of the prophylactic or therapeutic agents, or pharmaceutical compositions of the invention is packaged in a hermetically sealed container such as an ampoule or sachette indicating the quantity of the agent. In one embodiment, one or more of the prophylactic or therapeutic agents, or pharmaceutical compositions of the invention is supplied as a dry sterilized lyophilized powder or water free concentrate in a hermetically sealed container and can be reconstituted (e.g., with water or saline) to the appropriate concentration for administration to a subject. Preferably, one or more of the prophylactic or therapeutic agents or pharmaceutical compositions of the invention is supplied as a dry sterile lyophilized powder in a hermetically sealed container at a unit dosage of at least S mg, more preferably at least 10 mg, at least 15 mg, at least 25 mg, at least 35 mg, at least 45 mg, at least 50 mg, at least 75 mg, or at least 100 mg. The lyophilized prophylactic or therapeutic agents or pharmaceutical compositions of the invention should be stored at between 2° C. and 8° C. in its original container and the prophylactic or therapeutic agents, or pharmaceutical compositions of the invention should be administered within 1 week, preferably within 5 days, within 72 hours, within 48 hours, within 24 hours, within 12 hours, within 6 hours, within 5 hours, within 3 hours, or within 1 hour after being reconstituted. In an alternative embodiment, one or more of the prophylactic or therapeutic agents or pharmaceutical compositions of the invention is supplied in liquid form in a hermetically sealed container indicating the quantity and concentration of the agent. Preferably, the liquid form of the administered composition is supplied in a hermetically sealed container at least 0.25 mg/ml, more preferably at least 0.5 mg/ml, at least 1 mg/ml, at least 2.5 mg/ml, at least 5 mg/ml, at least 8 mg/ml, at least 10 mg/ml, at least 15 mg/kg, at least 25 mg/ml, at least 50 mg/ml, at least 75 mg/ml or at least 100 mg/ml. The liquid form should be stored at between 2° C. and 8° C. in its original container.

The antibodies and antibody portions of the invention can be incorporated into a pharmaceutical composition suitable for parenteral administration. Preferably, the antibody or antibody portions will be prepared as an injectable solution containing 0.1-250 mg/ml antibody. The injectable solution can be composed of either a liquid or lyophilized dosage form in a flint or amber vial, ampule or pre-filled syringe. The buffer can be L-histidine (1-50 mM), optimally 5-10 mM, at pH 5.0 to 7.0 (optimally pH 6.0). Other suitable buffers include but are not limited to, sodium succinate, sodium citrate, sodium phosphate or potassium phosphate. Sodium chloride can be used to modify the toxicity of the solution at a concentration of 0-300 mM (optimally 150 mM for a liquid dosage form). Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 2-4%). Stabilizers can be used in both liquid and lyophilized dosage forms, principally 1-50 mM L-Methionine (optimally 5-10 mM). Other suitable bulking agents include glycine, arginine, can be included as 0-0.05% polysorbate-80 (optimally 0.005-

0.01%). Additional surfactants include but are not limited to polysorbate 20 and BRIJ surfactants. The pharmaceutical composition comprising the antibodies and antibody-portions of the invention prepared as an injectable solution for parenteral administration, can further comprise an agent useful as an adjuvant, such as those used to increase the absorption, or dispersion of a therapeutic protein (e.g., antibody). A particularly useful adjuvant is hyaluronidase, such as Hylenex® (recombinant human hyaluronidase). Addition of hyaluronidase in the injectable solution improves human bioavailability following parenteral administration, particularly subcutaneous administration. It also allows for greater injection site volumes (i.e. greater than 1 ml) with less pain and discomfort, and minimum incidence of injection site reactions. (See International Appln. Publication No. WO 04/078140 and U.S. Patent Appln. Publication No. US2006104968, incorporated herein by reference.)

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies. The preferred mode of administration is parenteral (e.g., intravenous, subcutaneous, intraperitoneal, intramuscular). In a preferred embodiment, the antibody is administered by intravenous infusion or injection. In another preferred embodiment, the antibody is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antibody or antibody portion) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile, lyophilized powders for the preparation of sterile injectable solutions, the preferred methods of preparation are vacuum drying and spray-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including, in the composition, an agent that delays absorption, for example, monostearate salts and gelatin.

The antibodies and antibody portions of the present invention can be administered by a variety of methods known in the art, although for many therapeutic applications, the preferred route/mode of administration is subcutaneous injection, intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

In certain embodiments, an antibody or antibody portion of the invention may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Supplementary active compounds can also be incorporated into the compositions. In certain embodiments, an antibody or antibody portion of the invention is coformulated with and/or coadministered with one or more additional therapeutic agents that are useful for treating disorders in which PIVKA-II activity is detrimental. For example, an anti-PIVKA-II antibody or antibody portion of the invention may be coformulated and/or coadministered with one or more additional antibodies that bind other targets (e.g., antibodies that bind other cytokines or that bind cell surface molecules). Furthermore, one or more antibodies of the invention may be used in combination with two or more of the foregoing therapeutic agents. Such combination therapies may advantageously utilize lower dosages of the administered therapeutic agents, thus avoiding possible toxicities or complications associated with the various monotherapies.

In certain embodiments, an antibody to PIVKA-II or fragment thereof is linked to a half-life extending vehicle known in the art. Such vehicles include, but are not limited to, the Fc domain, polyethylene glycol, and dextran. Such vehicles are described, e.g., in U.S. patent application Ser. No. 09/428,082 and published International Patent Application No. WO 99/25044, which are hereby incorporated by reference for any purpose.

In a specific embodiment, nucleic acid sequences comprising nucleotide sequences encoding an antibody of the invention or another prophylactic or therapeutic agent of the invention are administered to treat, prevent, manage, or ameliorate a disorder or one or more symptoms thereof by way of gene therapy. Gene therapy refers to therapy performed by the administration to a subject of an expressed or expressible nucleic acid. In this embodiment of the invention, the nucleic acids produce their encoded antibody or prophylactic or therapeutic agent of the invention that mediates a prophylactic or therapeutic effect.

Any of the methods for gene therapy available in the art can be used according to the present invention. For general reviews of the methods of gene therapy, see Goldspiel et al., 1993, *Clinical Pharmacy* 12:488-505; Wu and Wu, 1991, *Biotherapy* 3:87-95; Tolstoshev, 1993, *Ann. Rev. Pharmacol. Toxicol.* 32:573-596; *Mulligan, Science* 260:926-932 (1993); and Morgan and Anderson, 1993, *Ann. Rev. Biochem.* 62:191-217; May, 1993, *TIBTECH* 11(5):155-215. Methods commonly known in the art of recombinant DNA technology which can be used are described in Ausubel et al. (eds.), Current Protocols in Molecular Biology, John Wiley &Sons, NY (1993); and Kriegler, Gene Transfer and Expression, A Laboratory Manual, Stockton Press, NY (1990). Detailed description of various methods of gene therapy are disclosed in U.S. Patent Application Publication No. US20050042664 A1 which is incorporated herein by reference.

Antibodies of the invention or antigen binding portions thereof can be used alone or in combination to treat diseases associated with the liver. For example, the antibody may be used as a targeted therapy to prevent autocline cancer growth, and may be attached to a toxic, chemotherapeutic agent (i.e., small molecule or large molecule having cytotoxic properties). Further, the antibody may be labeled for imaging purposes.

It should be understood that the antibodies of the invention or antigen binding portion thereof can be used alone or in combination with one or more additional agents, e.g., a therapeutic agent (for example, a small molecule or biologic), said additional agent being selected by the skilled artisan for its intended purpose. The additional agent also can be an agent that imparts a beneficial attribute to the therapeutic composition e.g., an agent that affects the viscosity of the composition.

It should further be understood that the combinations which are to be included within this invention are those combinations useful for their intended purpose. The agents set forth below are illustrative for purposes and not intended to be limited. The combinations, which are part of this invention, can be the antibodies of the present invention and at least one additional agent selected from the lists below. The combination can also include more than one additional agent, e.g., two or three additional agents if the combination is such that the formed composition can perform its intended function.

The pharmaceutical compositions of the invention may include a "therapeutically effective amount" or a "prophylactically effective amount" of an antibody or antibody portion of the invention. A "therapeutically effective amount" refers to an amount effective, at dosages and for periods of time necessary, to achieve the desired therapeutic result. A therapeutically effective amount of the antibody or antibody portion may be determined by a person skilled in the art and may vary according to factors such as the disease state, age, sex, and weight of the individual, and the ability of the antibody or antibody portion to elicit a desired response in the individual. A therapeutically effective amount is also one in which any toxic or detrimental effects of the antibody, or antibody portion, are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of an antibody or antibody portion of the invention is 0.1-20 mg/kg, more preferably 1-10 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

It will be readily apparent to those skilled in the art that other suitable modifications and adaptations of the methods of the invention described herein are obvious and may be made using suitable equivalents without departing from the scope of the invention or the embodiments disclosed herein. Having now described the present invention in detail, the same will be more clearly understood by reference to the following examples, which are included for purposes of illustration only and are not intended to limit the scope of the invention.

EXAMPLES

Example I

Development of 3C10 Cell Line

Design of immunogen: Fifteen mer peptides in the PIVKA-II (i.e., Protein induced by Vitamin K in absence of blood coagulation Factor II) specific region of PIVKA-II 13-27 were selected as immunogens. There were 6 decarboxylated amino acids of Glutamic acid in the 15 mer peptide in PIVKA-II, while prothrombin (factor-II) had 6 carboxylated glutamic acid (GLA) in the 15 mer peptide. The PIVKA-II specific 15 mer peptide, with a linker at the N-terminus wherein the linker was x-LERECVEETCSYEEA (SEQ ID NO: 1) (disulfide bond between two cysteine)(x=epsilon-aminocaproic acid), conjugated with keyhole limpet hemocyanin (KLH) was designed as the immunogen. Synthesis of the peptide and conjugation to the KLH was conducted with a standard method. The N-terminal region of the peptide was bound to the KLH.

Immunization: Peptide KLH was used to immunize wild type Balb/c, wild type C57BL/6 mice, germinal center-associated DNA primase (GANP) transgenic Balb/c mice, and GANP transgenic C57BL/6 mice. The method of GANP transgenic mice production and method of immunization were followed in accordance with the method described in Sakaguchi et. al., *The Journal of Immunology* 174 (2005), pages 4485-4494.

Reactivity determination to PIVKA-II and Prothrombin: PIVKA-II antigen was prepared by heating dried prothrombin powder (Sigma F5132) at 110° C. for 8 hours. (See Bajaj et. al., *J. Biol. Chem.* (Apr. 10, 1982), 257(7), pages 3726-31.) After more than 8 weeks from immunization, mouse serum was bled and reactivity to PIVKA-II and reactivity to prothrombin were determined using the following procedures:

Five ug/mL of PIVKA-II or 5 ug/mL of Prothrombin were added into the 96 wells of an Enzyme Immunoassay (EIA) plate, and PIVKA-II or prothrombin was coated onto the well surface. After blocking by blocking solution (give a manufacturer and location?), mouse serum was diluted and then added to the wells. After a washing step, anti-mouse antibody labeled by horseradish peroxidase (HRP) was added. After another washing step, substrate solution was added, and then absorbance was measured by spectrophotometer. Mice that showed the highest reactivity to PIVKA-II and the lowest reactivity to Prothrombin in each group were selected for the next step.

Fusion: Spleen cells from the 4 mice selected from each group of wild type Balb/c, wild type C57BL/6, GANP transgenic Balb/c, and GANP transgenic C57BL/6 were fused to myeloma cells with a standard method as described in Sakaguchi et. al., *The Journal of Immunology* 174 (2005), pages 4485-4494. The hybridoma cells were diluted by a limiting dilution method, and then the culture supernatant was used for the screening of the hybridomas.

Screening of Hybridoma: Screening of the hybridomas was performed by use of the following procedures:

One ug/mL of PIVKA-IL or 5 ug/mL of Prothrombin was added into the 96 well EIA plate, and PIVKA-II or Prothrombin was coated onto the well surface. After blocking by a solution including Block Ace, supernatants of the hybridomas were then added to the wells. After a washing step, anti-mouse antibody labeled by horseradish peroxidase was added. After another washing step, substrate solution was added and then absorbance was measured by spectrophotometer. The top 5 hybridomas in each group were selected by the following criteria: (1) no reactivity to prothrombin and then (2) top 5 reactivity to PIVKA-II (see FIG. 1.) There were no hybridomas obtained from wild type mice that reacted with PIVKA-II strongly. Hybridoma #3C10 from GANP transgenic C57BL/6 showed strong reactivity to PIVKA-II and no reactivity to prothrombin. It was thought that the method using GANP transgenic mouse with PIVKA-II peptide as immunogen could produce clones that produced antibody which had higher reactivity to PIVKA-II than wild mouse as well as no reactivity to the prothrombin.

Establishment of Clones: Cloning of hybridomas #3C10 and #2H4 were conducted using a standard procedure as described in Sakaguchi et. al., *The Journal of Immunology* 174 (2005), pages 4485-4494. Clones of 3C10 and 2H4 were then established.

Using the same procedures of fusion, screening of hybridomas and establishment of clones as described above for one of each group of GANP transgenic Balb/c and GANP transgenic C57BL/6 mice, clone #12D6 from GANP transgenic C57BL/6 mouse and clone #7B10 from GANP transgenic Balb/c mouse were established. These clones had strong reactivity to PIVKA-II and no reactivity to Prothrombin.

Example II

Hybridoma Screening with Automated Immunoassay of Architect System

Automated Immunoassay: Each hybridoma was cultured in serum free media. Antibodies in the culture supernatant were purified with a Protein A column. The antibodies were coated to the magnetic microparticles. (A carboxyl group was attached to the surface of the microparticles (Abbott Laboratories, IL) with a covalent bond using 1-Ethyl-3-[3-dimethylaminopropyl]carbodiimide hydrochloride (EDC).) The coated microparticles were dispersed into the buffer solution which included bovine serum albumin (BSA) and then Reagent A was prepared. Anti-Prothrombin antibody (code #PA150) from Hyphen Biomed (France) was labeled by N-hydroxysuccinimide (NHS) activated acridinium ester (Abbott Laboratories, IL). The labeled antibody was diluted into the buffer containing BSA, and then Reagent B was prepared. Buffer solution including Triton X-100 was prepared as Reagent C. The immunoassay was automatically conducted with the following procedures utilized with the automated immunoassay system of ARCHITECT i2000 (Abbott Laboratories, IL). In particular, 50 uL of Reagent A and 50 uL of reagent C were mixed with 50 uL of sample. The mixture was incubated at 37° C. for 18 minutes to allow binding of antibody coated on the magnetic microparticles and reactive substance (PIVKA-II) in the sample. Magnetic microparticles were attracted by a magnet and then the residual solutions were removed. The magnetic microparticles were washed by phosphate buffered saline (PBS) so that impurities nonspecifically bound on the magnetic microparticle surface were removed. Fifty uL of Reagent B was then added to the microparticle and then the complex of (antibody coated magnetic microparticle)—(PIVKA-II in sample)—(acridinium labeled antibody) was formed. After a washing step by PBS, peroxide was added in the alkaline condition, and then acridinium ester produced a luminescent signal which was detected by a photo multiplier tube (PMT).

Figure 2:
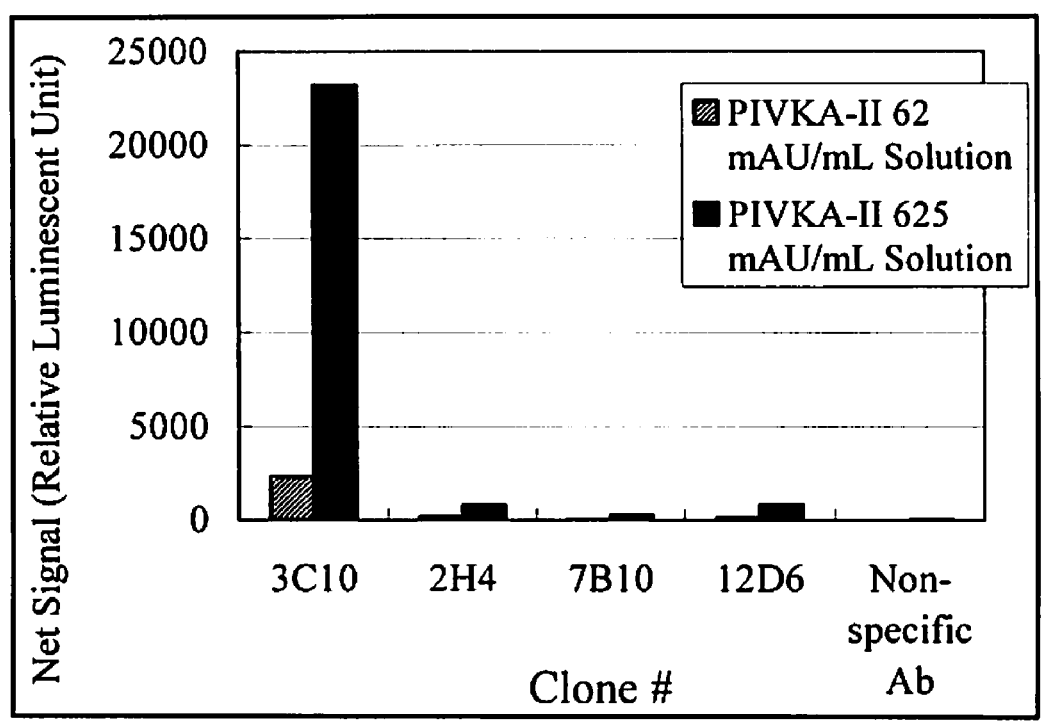
FIG. 2 shows the signals of the antibodies developed in Example III. Monoclonal antibody 3C10 showed the strongest reactivity to the PIVKA-II antigen.

PIVKA-II solution was tested with the Architect immunoassay using the 4 antibodies coated on the magnetic microparticles (FIG. 2). Clone 3C10 showed the strongest reactivity to the PIVKA-II antigen. These results indicated that 3C10 antibody showed high specificity for PIVKA-II and was highly reactive with PIVKA-II.

The cell line of the present invention (i.e., PIVKA-II 3C1D-129 p16 (which produces monoclonal antibody 3C10)) was deposited with the American Type Culture Collection, 10801 University Boulevard, Manassas, Va. 210110-2209, United States of America on Nov. 25, 2008 under the terms of the Budapest Treaty and has received deposit designation PTA-9638.

Example III

Figure 3:
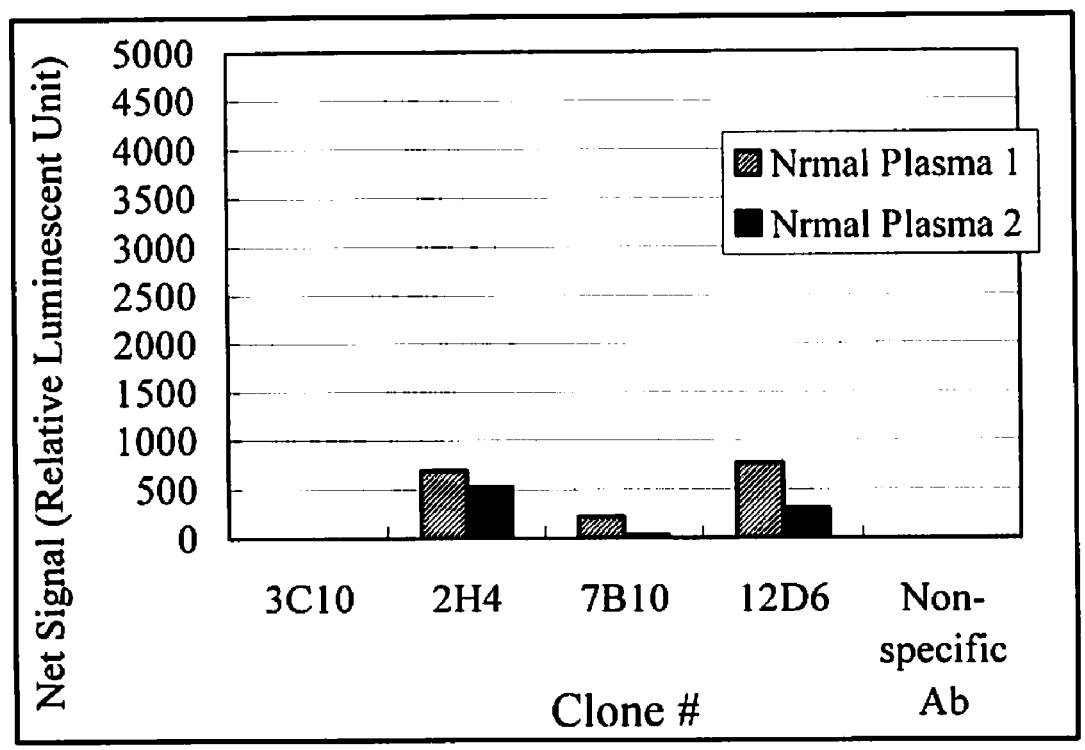
FIG. 3 shows the subtracted PIVKA-II signal and background in connection with the procedure noted in Example II.
Figure 4:
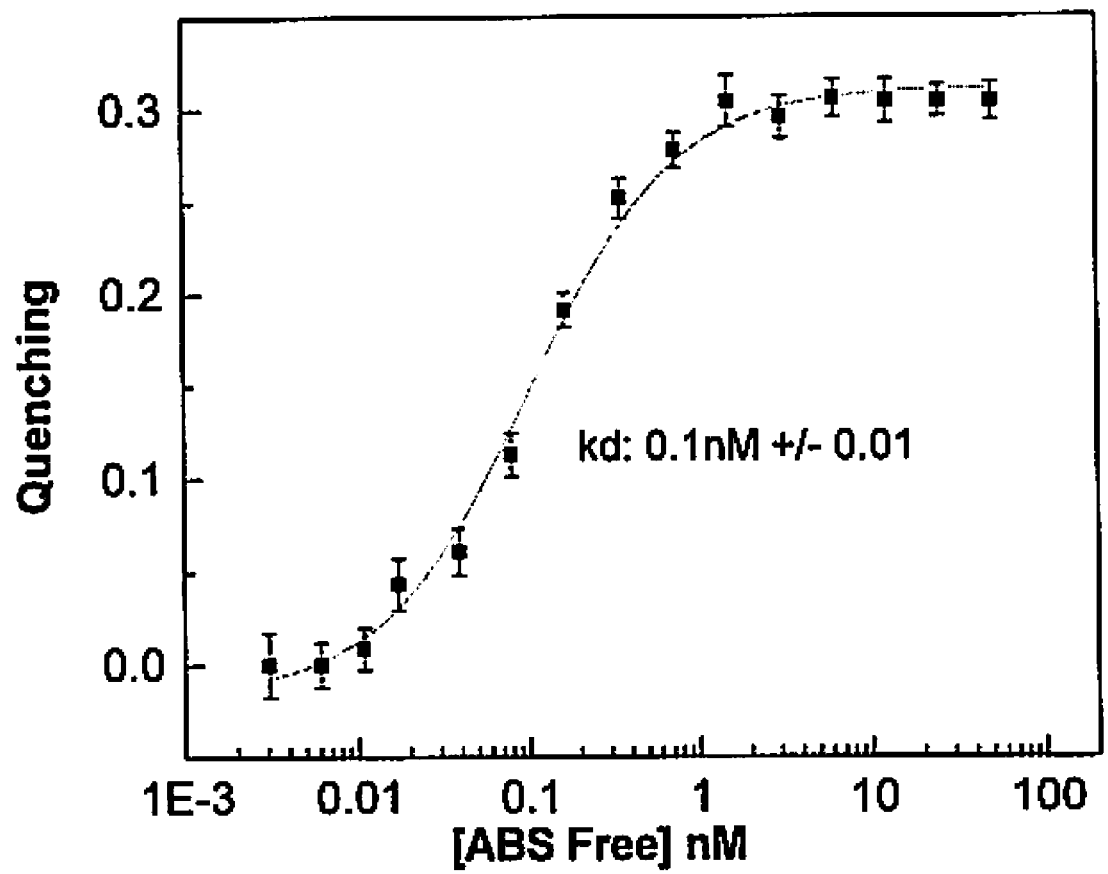
FIG. 4 illustrates the equilibrium dissociation constants ($K_d$) of antigens measured in direct binding experiments. Alexa-488 labeled PIVKAII Gla domain peptide (13-27) was kept at 0.05 nM, while the concentration of BHQ-mAb varied from 50 nM to 0.0002 nM. The total fluorescence signal of Alexa488-peptide was quenched 30% upon the binding of BHQ labeled antibody. The binding curve was fit with a simple fitting model.
Figure 5:
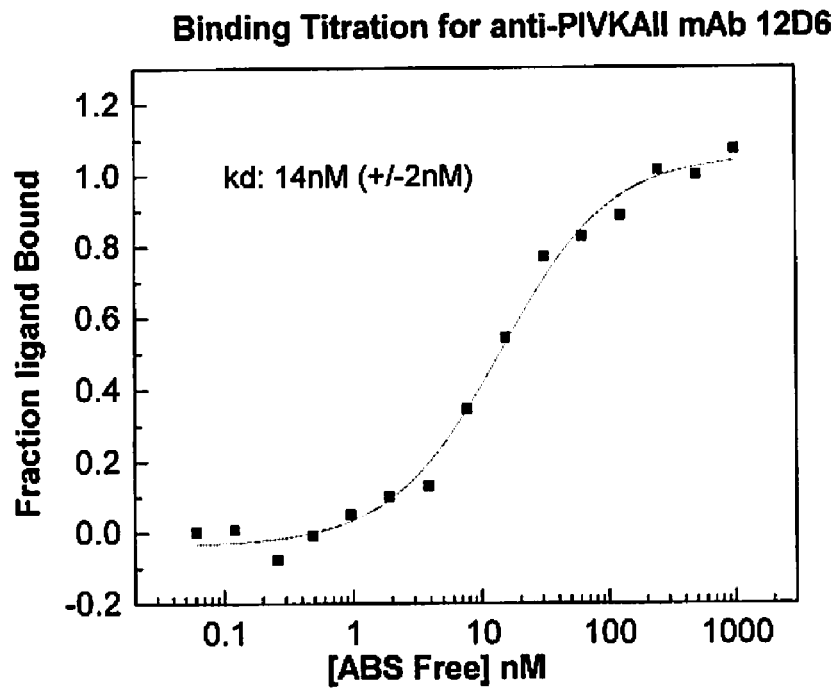
FIG. 5 illustrates the equilibrium dissociation constants ($K_d$) of antigens measured in direct binding experiments. Alexa-488 labeled PIVKAII Gla domain peptide (13-27) was kept at 0.2 nM, while the concentration of mAbs varied from 1 µM to sub nano-molar. Change in anisotropy is used to calculate fraction of ligand bound. The binding curve was fit with a simple fitting model (see Tetin, S. Y. and T. L. Hazlett (2000), "Optical spectroscopy in studies of antibody-hapten interactions," Methods 20(3):341-361).
Figure 5:
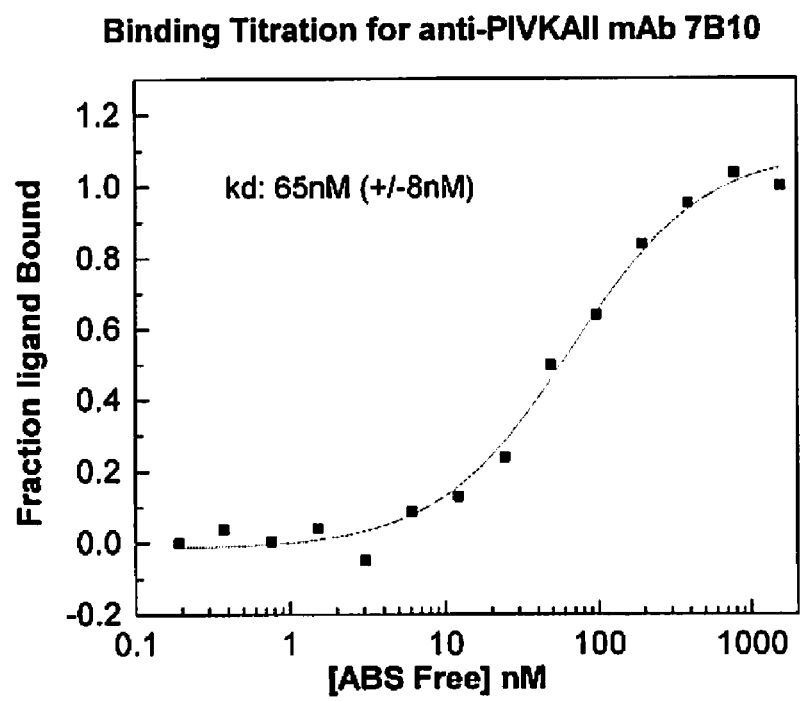

Reactivity of Clone 3C10, 2H4, 7B10 AND 12D6 to Plasma Substances using an Automated Immunoassay Two normal plasma specimens known to have the PIVKA-II value of 23 mAU/mL and 23.5 mAU/mL were tested with the Architect immunoassay using the 4 antibodies from clone #3C10, 2H4, 7B10, and 12D6 coated on the magnetic microparticles. Clone 3C10 and 7B10 showed no or little signal from the plasma (FIG. 3). This result indicated that 3C10 and 7B10 had no cross reactivity to the plasma substances including Factor II (Prothrombin), Factor IX, Factor X, Factor VII, Protein C, Protein S, and Protein Z. In particular, since Factor II is the precursor of PIVKA II Factor HH and has a GLA domain that contains carboxylated glutamic acid, and these amino acids are absent in PIVKA II, the antibody 3C10 is specific to these changes and does not recognize Factor II/prothrombin. Other coagulation factors such as Factor IX, Factor X and Factor VII also contain the GLA domain with a few amino acids being preferentially different (i.e., homologous proteins). Hence, the antibody 3C10 does not recognize any of these proteins although they are very similar in amino acid sequence to PIVKA II.

Example IV

Characterization of the Antibodies a) Material and Methods:
Sequences of the peptides synthesized (SEQ ID NOS: 1-2, respectively, in order of appearance):

| Peptide sequence for immunization | | | | | | | | | | | | | | | |
|---|---|---|---|---|---|---|---|---|---|---|---|---|---|---|---|
| | 13 | 14 | 15 | 16 | 17 | 18 | 19 | 20 | 21 | 22 | 23 | 24 | 25 | 26 | 27 |
| | | | | | Epitope of MU-3** | | | | | | | | | | |
| PIVKA-II | L | E | R | E | C | V | E | E | T | C | S | Y | E | E | A |
| Human Prothrombin | L | E* | R | E* | C | V | E* | E* | T | C | S | Y | E* | E* | A |

E*: 4-carboxyglutamic acid = Gla
**Reference: T. Naraki et. al., Biochimica et Biophysica Acta
**Complete citation: Naraki et al., Biochimica et Biophysica Acta, (2002), 1586, pages 287-298.

Peptides synthesized to evaluate the epitope specificity of the length of the peptide.

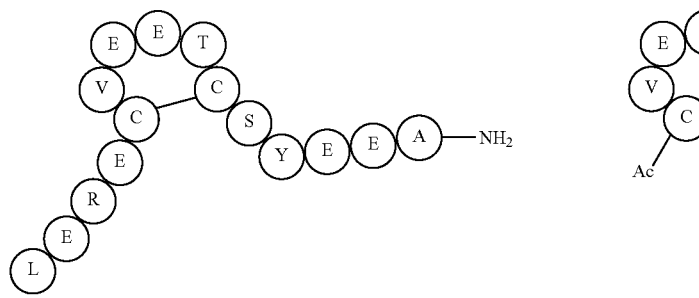

Cyclized PIVKAII peptide
(SEQ ID NO: 1)

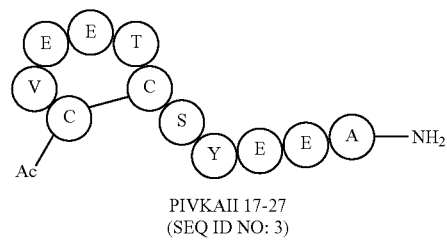

PIVKAII 17-27
(SEQ ID NO: 3)

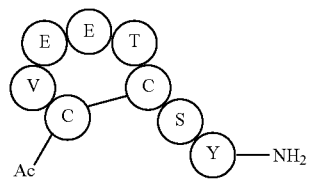

PIVKAII 17-24
(SEQ ID NO: 4)

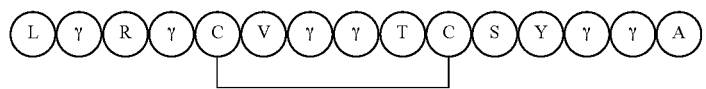

Prothrombin 13-27 SEQ ID NO: 2

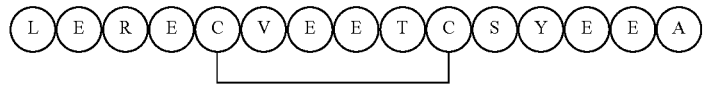

PIVKAII 13-27 SEQ ID NO: 1

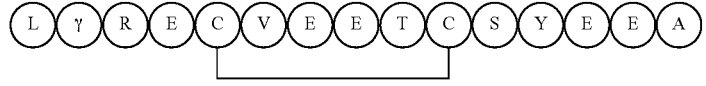

PIVKAII 13-27 GLA 14 SEQ ID NO: 5

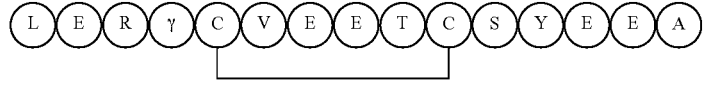

PIVKAII 13-27 GLA 16 SEQ ID NO: 6

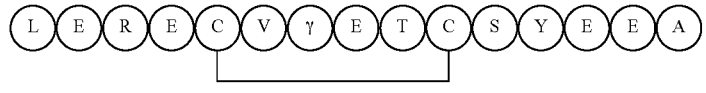

PIVKAII 13-27 GLA 19 SEQ ID NO: 7

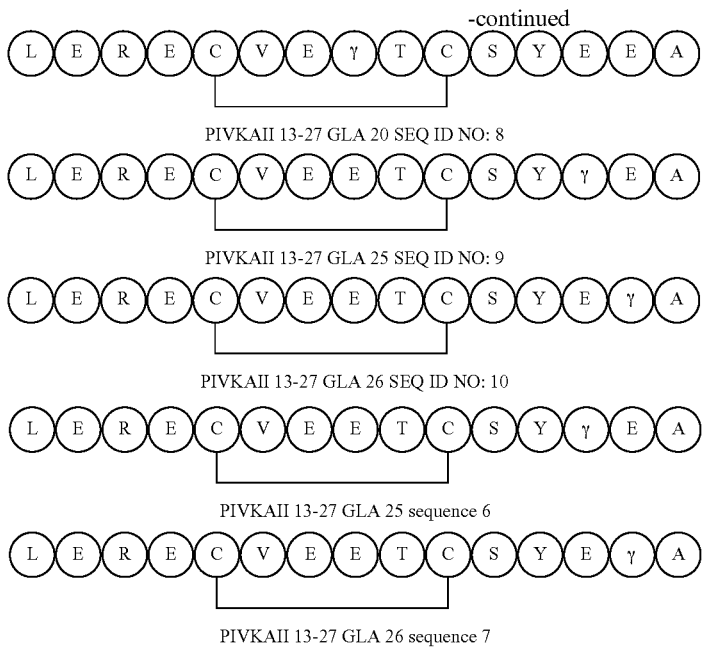

The above sequences are SEQ ID NOS 2, 1 and 5-10, respectively.

Homologous Series of Peptides
The variable residues are shown in bold:

```
LERECMEEKCSFEEA    (Gla domain Factor IX sequence 11)
(SEQ ID NO: 11)

LERECMEETCSYEEA    (Gla domain Factor X sequence 12)
(SEQ ID NO: 12)

LERECKEEQCSFEEA    (Gla domain Factor VII sequence 13)
(SEQ ID NO: 13)

LERECIEEICDFEEA    (Gla domain Protein C sequence 14)
(SEQ ID NO: 14)

LERECIEELCNKEEA    (Gla domain Protein S sequence 15)
(SEQ ID NO: 15)

LEKECYEEICVYEEA    (Gla domain Protein Z sequence 16)
(SEQ ID NO: 16)

LERECVEETCSYEEA    (PIVKA-II SEQUENCE)
(SEQ ID NO: 17)
``` b) Example of sequence homology analysis using Biology workbench: The GLA domain of prothrombin has sequence homology with other co-aggulation proteins. The protein sequence of Prothrombin, Protein Z, Protein S, Protein C, Factor X and Factor IX were retrieved from the Swiss-pro database and the GLA domain of these proteins was copied and fed into Biology workbench software (San Diego Supercomputer Center (SDSC), La Jolla, Calif.) for sequence alignment. The sequence alignment showed homology in the region of interest (i.e., 13 to 27) embedded in the GLA region of Prothrombin.

c) Peptide Synthesis: Peptides were synthesized using commercially available Fmoc protected amino acids on a Pioneer peptide synthesizer from ABI (Foster City, Calif.) or using a CS Bio synthesizer (Menlo Park, Calif.). The amino acids were activated with coupling reagents such as PyBOP (i.e., benzotriazol-1-yl-osytripyrrolidinophsphonium hexafluorophosphate) or PyAOP (i.e., 7-azabenzotriazol-1-yloxy-tris-(pyrrolidono)phosphonium hexafluorophosphate) The Fmoc protection was removed on the instrument, and the N-terminal amine was not capped. The peptides were cleaved using 2.5% water, 2.5% tri-isopropyl silane, and 95% TFA (i.e., trifluroacetic acid) reagent mixture for 1-2 hrs at room temperature. The cleaved peptide was precipitated with ether, dissolved in 50% aq. acetonitrile, and lyophilized to obtain the required peptide. This is the general procedure that was utilized for peptide synthesis for sequences #1 to 20. (See below.)

d) Cyclization of PIVKA-II: 50 mg diAcm PIVKA-II peptide (13-27) was mixed in 20 mL of acetic acid ("AcOH"): $H_2O$ mixture, (1:1 v/v). Two mL of 1N HCl was added followed by addition of 30 milligrams of iodine as a solution in 1 mL of methanol ("MeOH"):AcOH (1:1 v/v)(Greg Fields ed., Methods in Enzymology, Vol. 289, pp. 198-221, 1997). The reaction mixture was stirred for 45 minutes under dark conditions. The reaction mixture was a clear brown solution without any suspended particles. After 45 minutes, the reaction was quenched by adding a 10% solution of ascorbic acid. In particular, approximately 100 mg of an ascorbic acid solution (i.e., approximately 10 mL) was added (which is commercially available from Aldrich, Milwaukee, Wis.) dropwise until the solution was clear. The solution was diluted 4 times with water and purified by preparative HPLC. A Phenomenex Luna 10 u, C18(2) 250×50 mm column (Phenomenex, Torrance, Calif.) was used for purification, using a gradient of acetonitrile water (10-40%) for 60 minutes. The peptide was collected in fractions as the peak rose, and the fractions were checked by HPLC. The fractions with the highest purity (i.e., >98%) were pooled and lyophilized. One hundred and ten mgs of cyclized cyclized PIVKAII peptide (13-27) were obtained.

e) Labeling of PIVKAII Peptide: To prepare the Alexa 488 PIVKA-II peptide (13-27), 4 mg of cyclized PIVKA-II (13-27) were weighed into a 4 mL glass vial and treated with 2 mg of Alexa Flur 488 TFP active ester in 1 mL of DMF (i.e., dimethylformide). To this mixture was added 0.2 mL of DIEA (i.e., diisopropylethylamine) and the mixture was incubated for 2 hrs. The Alexa488 PIVKA-II peptide (13-27) was purified on a Phenomenex Luna 10 u, C18(2) 250×50 mm column (Phenomenex, Torrance, Calif.) using a gradient of acetonitrile water (10-40%) for 60 minutes. The pure fraction of the peak was pooled and lyophilized to obtain 0.6 mg of the dry powder. The concentration of labeled peptide was determined by absorption in 1 cm cuvette using $\Sigma_{495}$=71000 $M^{-1}$ $cm^{-1}$.

f) Labeling of the Antibody: Anti-PIVKA-II mAb 3C10 was selectively labeled with Black Hole Quencher (BHQ, Biosearch Technologies, Inc. Novato, Calif.). Purification and labeling procedures were provided by the vendor. The unlabeled BHQ-10s were removed on a G-25 column equilibrated with PBS. The concentrations of the labeled mAbs were determined using $\Sigma_{280}$=218000 $M^{-1}$ $cm^{-1}$, with corrections for contributions from BHQ (218000 $M^{-1}$ $cm^{-1}$). The molar incorporation ratio (I.R. dye/protein) was calculated based on the concentration of the protein and chromophore. The I.R. for mAb 3C10 is 2.3.

g) Fluorescence-based methods: Fluorescence anisotropy and förster resonance energy transfer (FRET) were used to determine the dissociation constants of Alexa-488 labeled PIVKA-II Gla domain peptide (13-27) and monoclonal antibodies developed against this peptide. In particular, fluorescence correlation spectroscopy (FCS) was used to compare the binding strength of the Gla-substituted PIVKA-II peptide (13-27) mutants and identify the epitopic Gla residues of the PIVKA-II peptide (13-27). FCS is a solution phase, single molecule level fluorescence technique that can measure the diffusion coefficient of fluorescent molecule. Large differences in the molecular masses of the free and antibody bound Alexa488-PIVKAII (13-27) results in a substantial change in diffusion coefficient, which in turn can be used to monitor the analyte and antibody interactions.

Instrumentation: All equilibrium fluorescence measurements were performed on an SLM 8100 photon counting spectrofluorimeter (SLM; no longer in existence). For anisotropy measurement, samples were excited at 480 nm, and emission fluorescence signals were collected through a polarizer and a 530/30 nm interference filter. Anisotropy values for each sample were measured 5 times, and the average value was recorded. For fluorescence intensity measurements, samples were excited at 480 nm. Total emission fluorescence signals were collected through a 530/30 nm interference filter (polarizer removed to improve sensitivity). Total fluorescence signals for each sample were measured 5 times, and the average value was recorded.

FSC experiments were performed using a dual-channel fluorescence correlation spectrometer ALBA (ISS, Champaign, Ill.) integrated with an inverted Nikon Eclipse TE300 fluorescence microscope (Nikon InsTech Co., Ltd., Kanagawa, Japan). Detailed information is described in Tetin et al., Biochemistry, 2006, 45:14155-65.

Determination of the Dissociation Constants: The equilibrium dissociation constants ($K_d$) of antigens (with the antibody of interest) were measured in direct binding experiments by monitoring changes in fluorescence anisotropy or fluorescence intensity. The Alexa-488 labeled antigen was kept at concentrations well below the $K_d$, while the antibodies' concentration incrementally increased from the picomolar range to sub-micromolars in the series of 15 samples.

Since there is no fluorescence intensity quenching of Alexa488-antigen when it binds to the antibody, the change in anisotropy is directly proportional to the fraction of antigen bound to antibody (Fb) as follows:

$$Fb(i) = \frac{A(i) - A\min}{A\max - A\min} \tag{1}$$

where $A_{(i)}$ is the anisotropy of Alexa488-antigen at each antibody concentration, $A_{min}$ is the anisotropy of Alexa488-antigen alone, and $A_{max}$ is the anisotropy of antibody bound Alexa488-antigen. The concentration of the unbound antibody binding sites $[ABS_{free}]$ can be calculated from the following formula:

$$[ABS_{free}] = [ABS_{total}] - [T_{total}] \times Fb \tag{2}$$

The binding data were then fitted with the simple binding model to calculate the equilibrium dissociation constant. $K_d$:

$$Fb = \frac{[ABS_{free}]}{K_d + [ABS_{free}]} \tag{3}$$

For high affinity monoclonal antibody 3C10 (mAb 3C10), a lower concentration of Alexa488-antigen (50 pM) is required for the binding measurement, which is below the sensitivity of anisotropy measurement. A different approach is therefore used. In particular, by introducing a Black-hole quencher (none fluorescent chromophore) onto the mAb 3C10, the fluorescence intensity of Alexa488-antigen is quenched upon its binding to mAb 3C10. The quenching (Q) of fluorescence intensity of the antigen (Ii) at each antibody concentration is calculated from equation 4.

$$Q = 1 - \frac{I_i}{I_{max}}, Q_{max} = 1 - \frac{I_{min}}{I_{max}} \tag{4}$$

where $I_{max}$ is the fluorescence intensity of the antigen in the absence of antibody. $I_{min}$ is the fluorescence intensity of the antigen at highest antibody concentration. Assuming that the value of $Q/Q_{max}$ can be directly translated into the fraction of Alexa488-antigen bound to its monoclonal antibody, the concentration of the unbound antibody binding sites $[ABS_{free}]$ can be calculated from the following formula:

$$[ABS_{free}] = [ABS_{total}] - [T_{total}] \times Q/Q_{max} \tag{5}$$

where $[ABS_{total}]$ and $[T_{total}]$ are the antibody binding sites and total concentrations of the Alexa488-peptide, respectively. The binding data were then fitted with the simple binding model to calculate the equilibrium dissociation constant. $K_d$:

$$Q = \frac{Q_{max} * [ABS_{free}]}{K_d + [ABS_{free}]} \tag{6}$$

All binding measurements were performed in 10 mM HEPES buffer, pH 7.4, containing 0.15M NaCl, 3mM EDTA, and 0.005% surfactant P20.

The bind titration curves of Alexa-488 labeled PIVKAII Gla domain peptide (13-27) and the mAbs are shown in FIGS.

4 and 5. The dissociation constants and changes in anisotropy of Alexa488—antigen upon its binding to mAbs are listed in Table I below:

TABLE I

|  | Kd (nM) | Anisotropy Changes |
| --- | --- | --- |
| mAb 1B9 | 92(+/−)12 | 0.05->0.17 |
| mAb 7B10 | 65(+/−)8 | 0.05->0.16 |
| mAb 12D6 | 14(+/−)2 | 0.05->0.14 |
| mAb 2H4 | 2(+/−)0.4 | 0.05->0.17 |
| mAb 3C10 | 0.15(+/−)0.1 | 0.05->0.095 |

Figure 6:
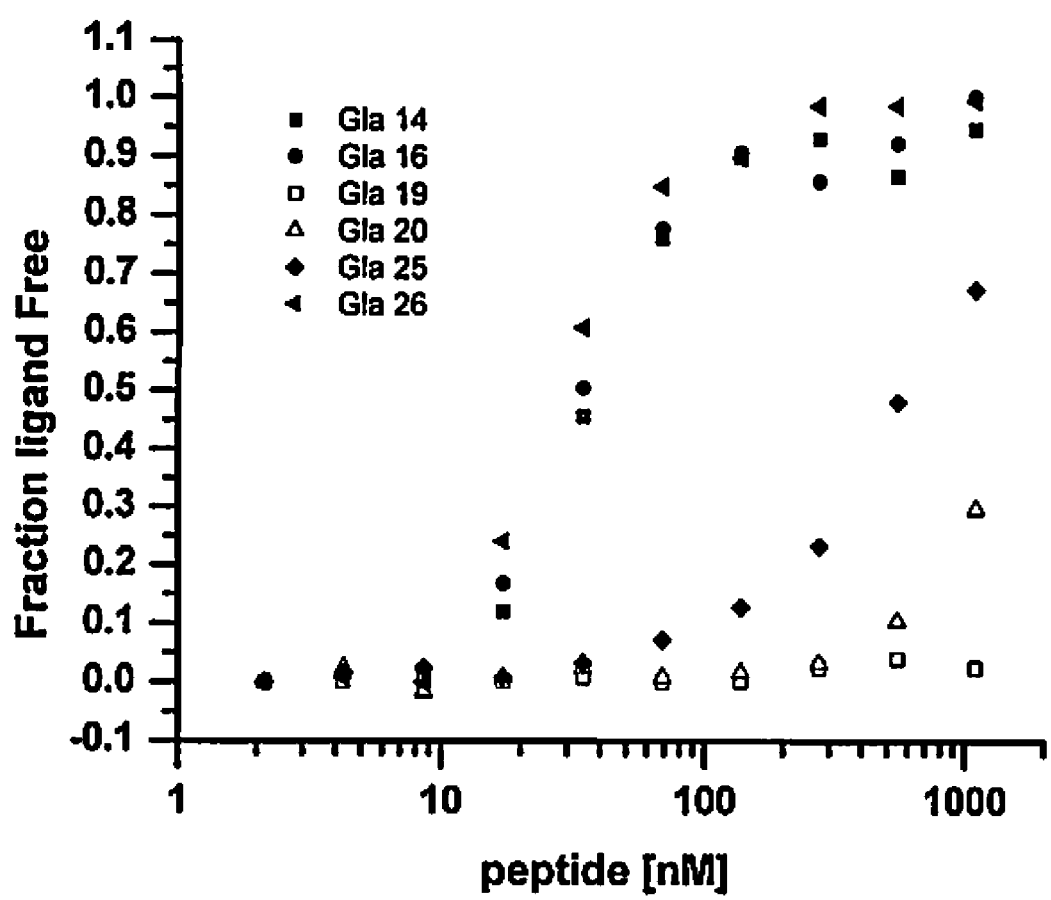
FIG. 6 illustrates FCS measurements of individual samples. In particular, 2 nM Alexa488-PIVKAII peptide (13-27 cyc) was premixed with 10 nM mAb 3C10. Various amounts of Glu-substituted peptide (Gla14, Gla 16, Gla 19, Gla 20, Gla 25, Gla26) were then added to the antigen-antibody complex. After overnight incubation, FCS measurements were performed on each sample. Changes in diffusion coefficient of Alexa488-PIVKAII (13-27) were used to calculate fraction of Alexa-488 PIVKAII peptide displaced by Glu-substituted peptides.

Epitope Mapping By Fluorescence Correlation Spectroscopy: The competitive binding measurements of Glu-substituted peptide with Alexa488-PIVKA-II (13-27) and mAb 3C10 identified specific Gla residues in the 13-27 region that play a critical role in epitope recognition for mAb 3C10. The results showed that residues Gla 19, 20 and 25 are involved in epitope recognition for mAb 3C10, as replacement with Glu at each of those positions partially or completely eliminates the recognition by the mAb 3C10 (see FIG. 6).

Figure 7:
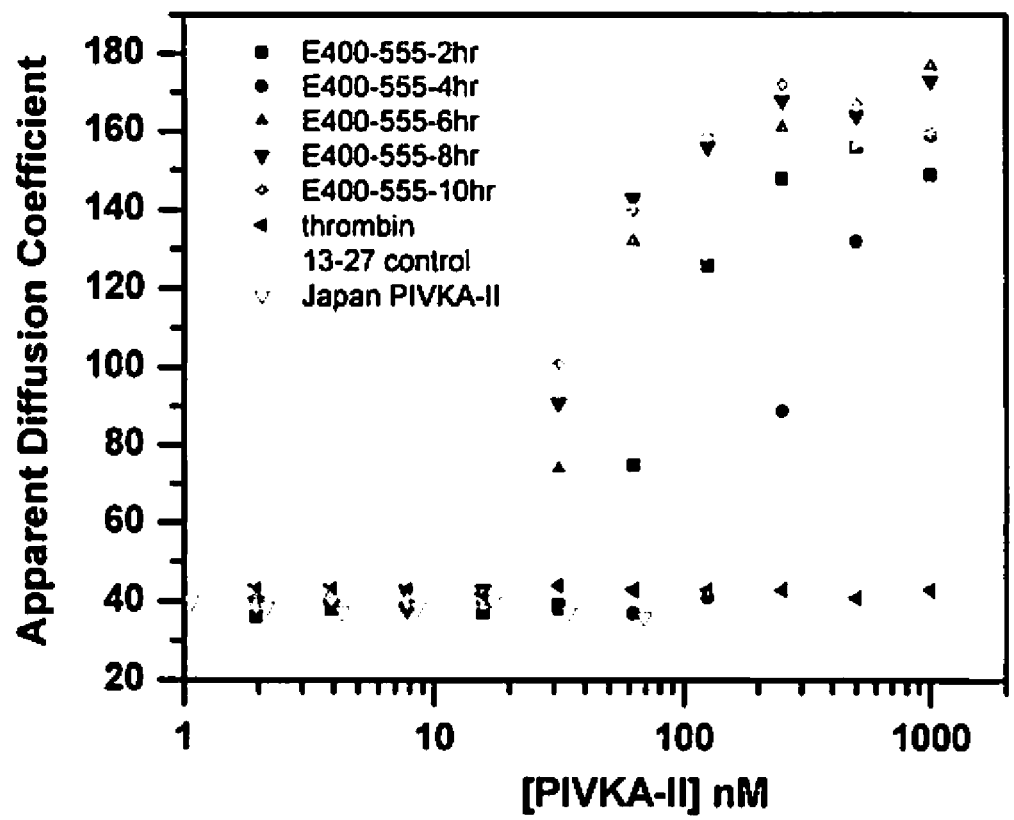
FIG. 7 illustrates additional FCS measurements of each sample. In particular, 2 nM Alexa488-PIVKAII peptide (13-27 cyc) was premixed with 1 nM mAb 3C10. Various amounts of PIVKAII from different preparations were added to the antigen-antibody complex. After overnight incubation, FCS measurements were performed on each sample. Changes in diffusion coefficient of Alexa488-PIVKAII (13-27) were used to calculate the fraction of Alexa-488 PIVKAII peptide displaced by PIVKAII.

Potency of Various Preparations of PIVKAII: Competitive binding measurements of various preparations of PIVKA-II with Alexa488-PIVKA-II (13-27) and mAb 3C10 were used to compare the potency of various lots of PIVKA-II. The results showed that, after 4 hours of heating, the potency of the sample reached its highest value and would not improve if heated longer than four hours (see FIG. 7).

Figure 8:
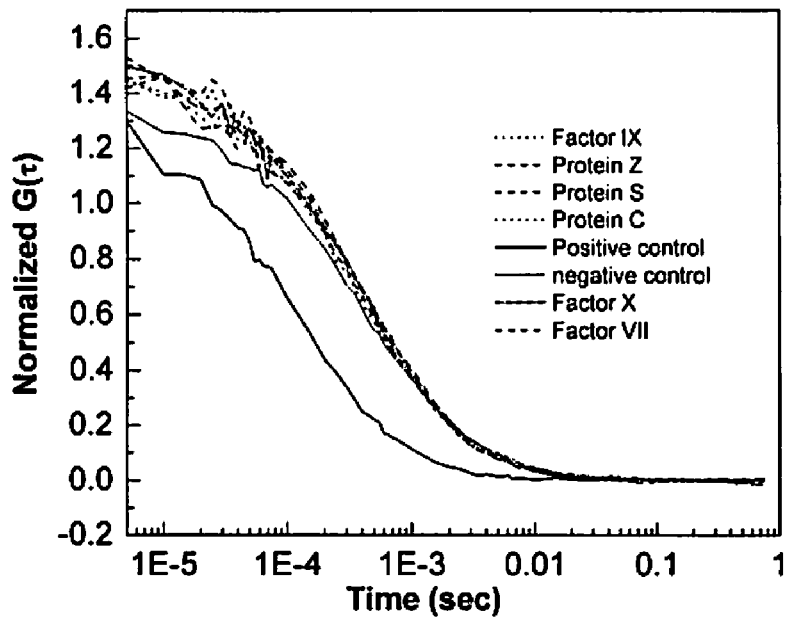
FIG. 8 illustrates the results obtained when competitive binding measurements of various PIVKAII Gla domain (13-27) analogs with Alexa488-PIVKAII (13-27) and mAb 3C10 were used to test cross-reactivity with mAb 3C10.

Cross-reactivity of PIVKA-II Gla Domain (13-27) Analog: Competitive binding measurements of various PIVKAII Gla domain (13-27) analogs with Alexa488-PIVKAII (13-27) and mAb 3C10 were used to test their cross-activity with mAb 3C10. 2 nM Alexa488-PIVKAII (13-27) and 10 nM mAb 3C10 were premixed to ensure all Alexa488-PIVKAII (13-27) were bound to the antibody. Then, various PIVKAII Gla domain (13-27) analogs were added to the sample. PIVKAII (13-27) was added as a positive control, and the original sample was used as a negative control. FCS measurements were performed on each sample after overnight incubation. FIG. 8 illustrates the auto-correlation curves from each sample and the calculated diffusion coefficient (D). The results showed that PIVKAII (13-27) can displace Alexa488-PIVKAII (13-27) from mAb 3C10, yielding a high D value; while all other PIVKAII peptide analog can not displace Alexa488-PIVKAII (13-27) from mAb 3C10, indicating they have no cross-reactivity with mAb3C10.

What is claimed is:

1. A hybridoma cell line designated by American Type Culture Collection (ATCC) deposit designation PTA-9638.

2. The monoclonal antibody produced by said hybridoma cell line of claim 1.

3. An isolated nucleic acid molecule fully encoding a binding protein which binds to PIVKA-II, wherein said binding protein comprises a variable heavy chain of said monoclonal antibody of claim 2.

4. The isolated nucleic acid molecule of claim 3, wherein said binding protein binds to amino acids 13-27 of PIVKA-II.

5. A purified protein fully encoded by said isolated nucleic acid molecule of claim 3, wherein said purified protein binds to PIVKA-II.

6. A vector comprising said isolated nucleic acid molecule of claim 3.

7. An isolated host cell comprising said vector of claim 6.

8. A method of producing a hybridoma cell line which expresses a binding protein comprising an antigen-binding domain which binds to amino acids 13-27 of PIVKA-II comprising the steps of:

a) immunizing a GANP mouse with an antigen comprising amino acids 13-27 of PIVKA-II for a time and under conditions sufficient for said mouse to produce antibodies against said antigen;

b) harvesting and purifying B cells from the spleen of said mouse;

c) fusing said spleen cells with myeloma cells in order to produce hybridomas; and d) selecting a hybridoma cell line which expresses said binding protein comprising an antigen-binding domain which binds to amino acids 13-27 of PIVKA-II, wherein said hybridoma cell line has ATCC deposit designation PTA-9638.

9. A pharmaceutical composition comprising the monoclonal antibody of claim 2 and a pharmaceutically acceptable carrier.

10. A kit comprising a container containing said monoclonal antibody of claim 2.

* * * * *

SEQUENCE LISTING

```
<160> NUMBER OF SEQ ID NOS: 17

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (5)..(10)

<400> SEQUENCE: 1

Leu Glu Arg Glu Cys Val Glu Glu Thr Cys Ser Tyr Glu Glu Ala
1               5                   10                  15

<210> SEQ ID NO 2
<211> LENGTH: 15
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: 4-carboxyglutamic acid
<220> FEATURE:
<221> NAME/KEY: MOD_RES
<222> LOCATION: (4)..(4)
<223> OTHER INFORMATION: 4-carboxyglutamic acid
<220> FEATURE:
<221> NAME/KEY: DISULFID
<222> LOCATION: (5)..(10)
<220> FEATURE:
<221> NAME/KEY: MOD_RES
<222> LOCATION: (7)..(8)
<223> OTHER INFORMATION: 4-carboxyglutamic acid
<220> FEATURE:
<221> NAME/KEY: MOD_RES
<222> LOCATION: (13)..(14)
<223> OTHER INFORMATION: 4-carboxyglutamic acid

<400> SEQUENCE: 2

Leu Xaa Arg Xaa Cys Val Xaa Xaa Thr Cys Ser Tyr Xaa Xaa Ala
1               5                   10                  15
```

```
<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(6)

<400> SEQUENCE: 3

Cys Val Glu Glu Thr Cys Ser Tyr Glu Glu Ala
1               5                   10

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(6)

<400> SEQUENCE: 4

Cys Val Glu Glu Thr Cys Ser Tyr
1               5

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: 4-carboxyglutamic acid
<220> FEATURE:
<221> NAME/KEY: DISULFID
<222> LOCATION: (5)..(10)

<400> SEQUENCE: 5

Leu Xaa Arg Glu Cys Val Glu Glu Thr Cys Ser Tyr Glu Glu Ala
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: 4-carboxyglutamic acid
<220> FEATURE:
<221> NAME/KEY: DISULFID
<222> LOCATION: (5)..(10)

<400> SEQUENCE: 6

Leu Glu Arg Xaa Cys Val Glu Glu Thr Cys Ser Tyr Glu Glu Ala
1               5                   10                  15

<210> SEQ ID NO 7
<211> LENGTH: 15
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: 4-carboxyglutamic acid
<220> FEATURE:
<221> NAME/KEY: DISULFID
<222> LOCATION: (5)..(10)

<400> SEQUENCE: 7

Leu Glu Arg Glu Cys Val Xaa Glu Thr Cys Ser Tyr Glu Glu Ala
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: 4-carboxyglutamic acid
<220> FEATURE:
<221> NAME/KEY: DISULFID
<222> LOCATION: (5)..(10)

<400> SEQUENCE: 8

Leu Glu Arg Glu Cys Val Glu Xaa Thr Cys Ser Tyr Glu Glu Ala
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: 4-carboxyglutamic acid
<220> FEATURE:
<221> NAME/KEY: DISULFID
<222> LOCATION: (5)..(10)

<400> SEQUENCE: 9

Leu Glu Arg Glu Cys Val Glu Glu Thr Cys Ser Tyr Xaa Glu Ala
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: 4-carboxyglutamic acid
<220> FEATURE:
<221> NAME/KEY: DISULFID
<222> LOCATION: (5)..(10)

<400> SEQUENCE: 10

Leu Glu Arg Glu Cys Val Glu Glu Thr Cys Ser Tyr Glu Xaa Ala
1               5                   10                  15
```

-continued

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Leu Glu Arg Glu Cys Met Glu Glu Lys Cys Ser Phe Glu Glu Ala
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Leu Glu Arg Glu Cys Met Glu Glu Thr Cys Ser Tyr Glu Glu Ala
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Leu Glu Arg Glu Cys Lys Glu Glu Gln Cys Ser Phe Glu Glu Ala
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Leu Glu Arg Glu Cys Ile Glu Glu Ile Cys Asp Phe Glu Glu Ala
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Leu Glu Arg Glu Cys Ile Glu Glu Leu Cys Asn Lys Glu Glu Ala
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 16

Leu Glu Lys Glu Cys Tyr Glu Glu Ile Cys Val Tyr Glu Glu Ala
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Leu Glu Arg Glu Cys Val Glu Glu Thr Cys Ser Tyr Glu Glu Ala
1               5                   10                  15
```